(12) United States Patent
Fourkas et al.

(10) Patent No.: US 6,197,016 B1
(45) Date of Patent: *Mar. 6, 2001

(54) DUAL VALVE, FLEXIBLE EXPANDABLE SHEATH AND METHOD

(75) Inventors: Michael G. Fourkas, Menlo Park; Steven G. Baker, Sunnyvale; David H. Mitchell, Cupertino, all of CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/346,036

(22) Filed: Jul. 6, 1999

Related U.S. Application Data

(63) Continuation of application No. 08/905,167, filed on Aug. 1, 1997, now Pat. No. 5,935,122, which is a continuation-in-part of application No. 08/534,393, filed on Sep. 27, 1995, now Pat. No. 5,653,697, which is a continuation of application No. 08/333,229, filed on Nov. 2, 1994, now Pat. No. 5,484,418, which is a division of application No. 08/109,131, filed on Aug. 19, 1993, now Pat. No. 5,395,349, which is a continuation-in-part of application No. 07/807,089, filed on Dec. 13, 1991, now Pat. No. 5,256,150.

(51) Int. Cl.[7] .................................................. A61M 25/16

(52) U.S. Cl. ........................... 604/537; 604/523; 604/248

(58) Field of Search .................................. 604/248, 171, 604/256, 523, 166.01, 170.01, 537, 167.01, 164.01, 165.01; 251/4, 345

(56) References Cited

U.S. PATENT DOCUMENTS

| | | |
|---|---|---|
| 1,986,484 | 1/1935 | Schlueter . |
| 2,844,351 | 7/1958 | Smith . |
| 3,825,001 | 7/1974 | Bennet et al. . |
| 3,868,956 | 3/1975 | Alfidi et al. . |
| 4,130,904 | 12/1978 | Whalen . |
| 4,306,318 | 12/1981 | Mano et al. . |
| 4,311,136 | 1/1982 | Weikl et al. . |
| 4,392,853 | 7/1983 | Muto . |
| 4,401,433 | 8/1983 | Luther . |
| 4,540,404 | 9/1985 | Wolvek . |
| 4,540,411 | 9/1985 | Bodicky . |
| 4,550,447 | 11/1985 | Seiler, Jr. et al. . |
| 4,580,473 | 4/1986 | Quinn . |

(List continued on next page.)

FOREIGN PATENT DOCUMENTS

| | | |
|---|---|---|
| 150281 | 8/1985 | (EP) . |
| 0249456 | 12/1987 | (EP) . |
| 0426407 | 5/1991 | (EP) . |
| 84/01512 | 4/1984 | (WO) . |
| 86/07267 | 12/1986 | (WO) . |

*Primary Examiner*—Sharon Kennedy
*Assistant Examiner*—Cris L Rodriguez
(74) *Attorney, Agent, or Firm*—Fulwider Patton Lee & Utecht, LLP

(57) ABSTRACT

A large-diameter expandable sheath for use in introducing a catheter or other medical instrument into a vessel in the body of a patient. The expandable sheath comprises an elongate sheath tube formed of a flexible material which has proximal and distal extremities and a passage extending therethrough of a maximum predetermined diameter. The distal extremity of the elongate sheath tube is folded longitudinally to a smaller folded diameter. The sheath tube may be self-expanding or may be reinforced with a self-expanding wire or expandable stents. A backflow adapter is secured to the proximal extremity of the elongate sheath tube. The backflow adapter has a central opening therein in registration with the passage in the sheath tube. A normally closed primary valve is disposed in the central opening of the backflow adapter and is movable to an open position. A normally open secondary valve, movable to a closed position, may be configured in the backflow adapter proximal the sheath tube and distal the primary valve. The primary and secondary valves when open permit a catheter or other medical instrument to be inserted into the sheath.

18 Claims, 18 Drawing Sheets

U.S. PATENT DOCUMENTS

| | | |
|---|---|---|
| 4,601,713 | 7/1986 | Fuqua . |
| 4,629,458 | 12/1986 | Pinchuk . |
| 4,665,906 | 5/1987 | Jervis . |
| 4,710,181 | 12/1987 | Fuqua . |
| 4,723,942 | 2/1988 | Scott . |
| 4,738,666 | 4/1988 | Fuqua . |
| 4,743,251 | 5/1988 | Barra . |
| 4,798,193 | 1/1989 | Giesy et al. . |
| 4,813,938 | 3/1989 | Raulerson . |
| 4,850,350 | 7/1989 | Jackson . |
| 4,857,062 | 8/1989 | Russell . |
| 4,895,565 | 1/1990 | Hillstead . |
| 4,929,235 | 5/1990 | Merry et al. . |
| 4,944,729 | 7/1990 | Buckberg et al. . |
| 4,969,896 | 11/1990 | Shors . |
| 4,990,143 | 2/1991 | Sheridan . |
| 5,015,239 | 5/1991 | Browne . |
| 5,025,778 | 6/1991 | Silverstein et al. . |
| 5,030,227 | 7/1991 | Rosenbluth et al. . |
| 5,066,285 | 11/1991 | Hillstead . |
| 5,066,298 | 11/1991 | Hess . |
| 5,092,846 | 3/1992 | Nishijima et al. . |
| 5,121,536 | 6/1992 | Pike . |
| 5,127,626 | 7/1992 | Hillal et al. . |
| 5,147,315 | 9/1992 | Weber . |
| 5,158,553 | 10/1992 | Berry et al. . |
| 5,167,636 | 12/1992 | Cleiment . |
| 5,176,652 | 1/1993 | Littrell . |
| 5,183,464 | 2/1993 | Dubrul et al. . |
| 5,184,627 | 2/1993 | de Toledo . |
| 5,190,528 | 3/1993 | Fonger et al. . |
| 5,195,991 | 3/1993 | Pike . |
| 5,211,370 | 5/1993 | Powers . |
| 5,213,093 | 5/1993 | Swindle . |
| 5,217,114 | 6/1993 | Gadberry et al. . |
| 5,226,193 | 7/1993 | Pinchuk . |
| 5,234,425 | 8/1993 | Fogarty et al. . |
| 5,242,399 | 9/1993 | Lau et al. . |
| 5,242,410 | 9/1993 | Melker . |
| 5,246,424 | 9/1993 | Wilk . |
| 5,256,150 | 10/1993 | Quiachon et al. . |
| 5,279,610 | 1/1994 | Park et al. . |
| 5,300,032 | 4/1994 | Hibbs et al. . |
| 5,378,237 | 1/1995 | Boussignac et al. . |
| 5,382,230 | 1/1995 | Bonn . |
| 5,383,860 | 1/1995 | Lau . |
| 5,389,031 | 2/1995 | Castro . |
| 5,395,349 | 3/1995 | Quiachon et al. . |
| 5,447,503 | 9/1995 | Miller . |
| 5,476,477 | 12/1995 | Burns . |
| 5,484,418 | 1/1996 | Quiachon et al. . |
| 5,653,697 | 8/1997 | Quiachon et al. . |
| 5,935,122 | 8/1999 | Fourkas et al. . |

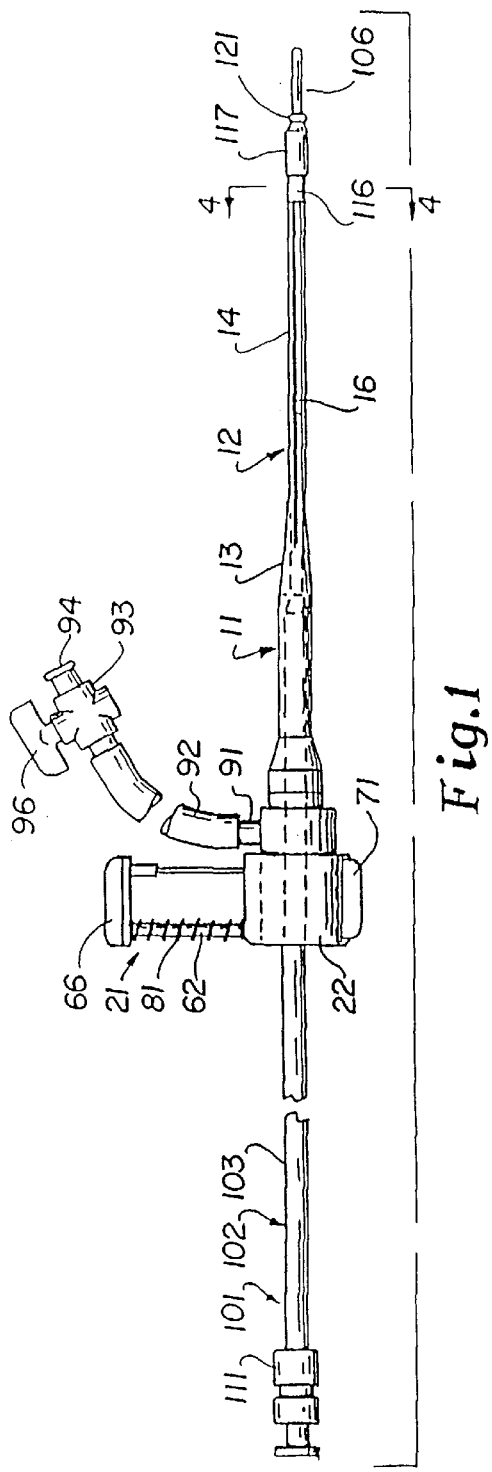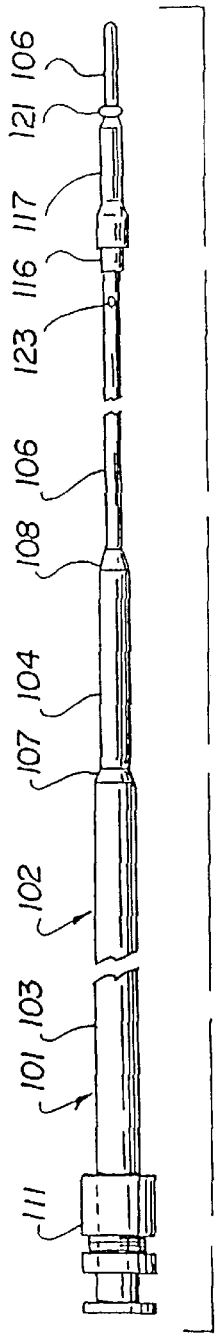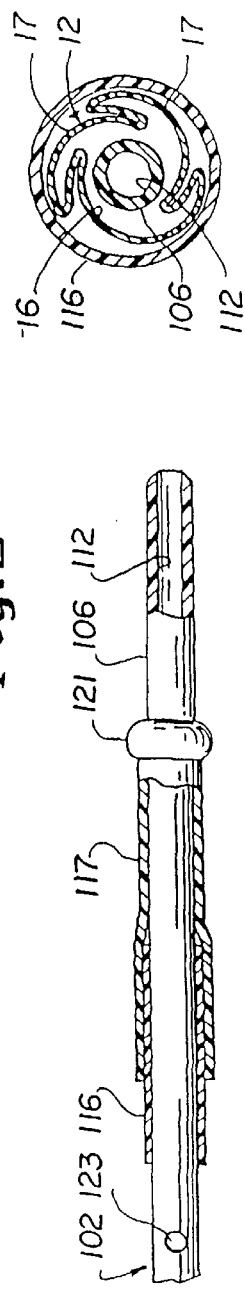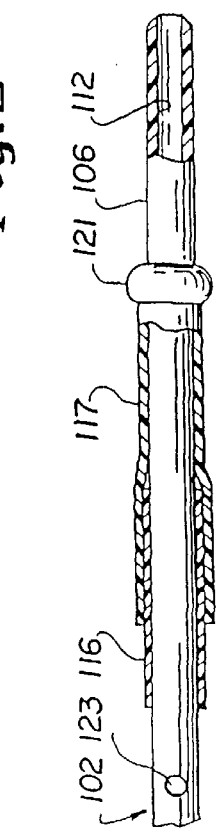

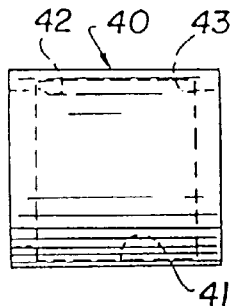
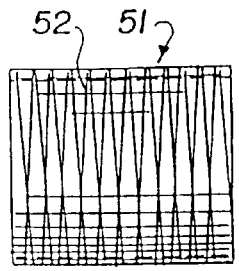
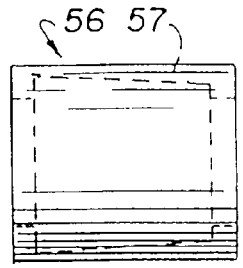
Fig.14　　　Fig.15　　　Fig.16
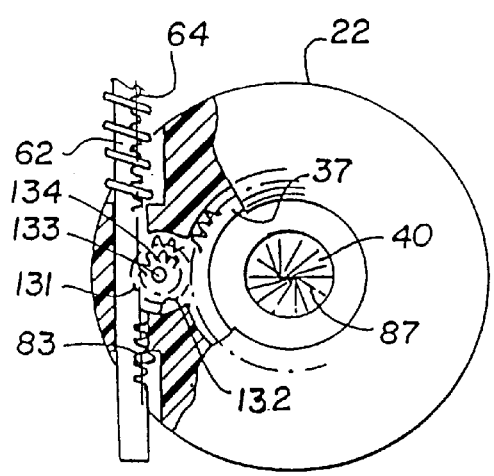
Fig.17
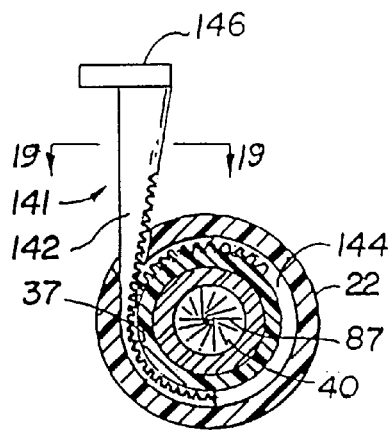
Fig.18
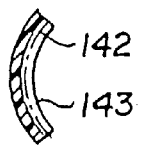
Fig.19

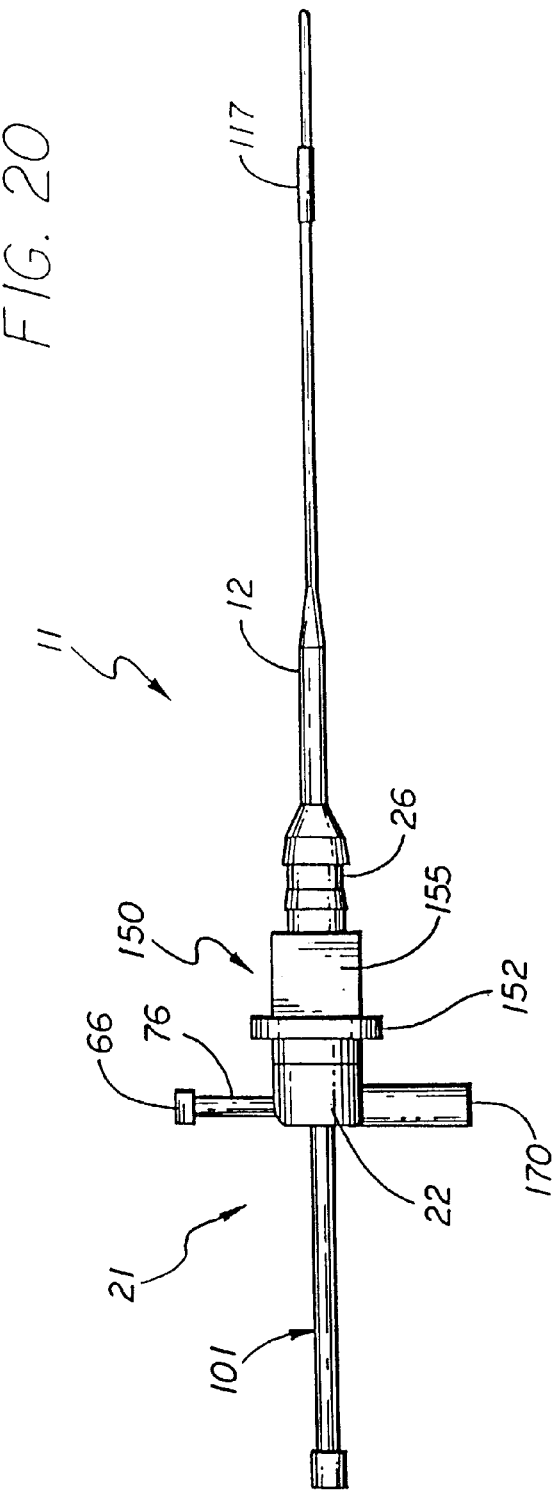
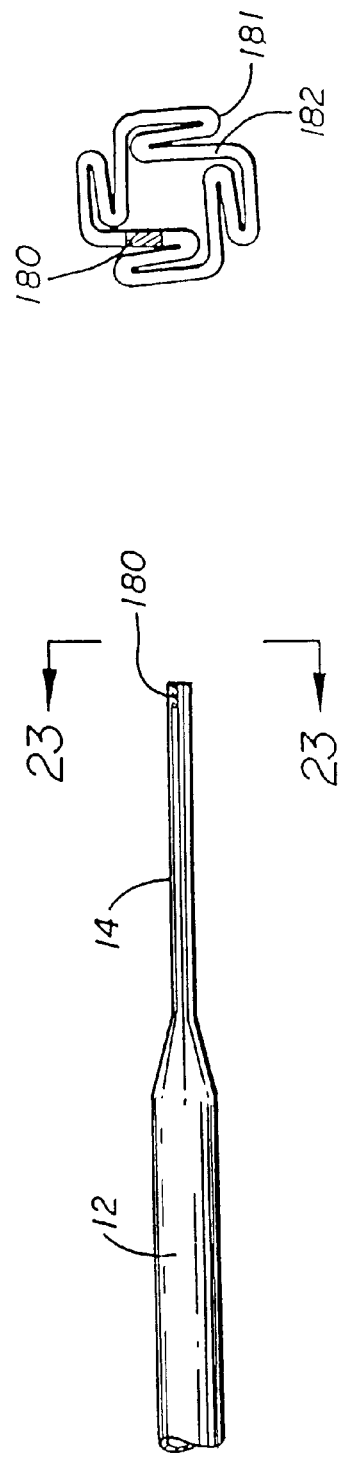

FIG. 24
FIG. 25
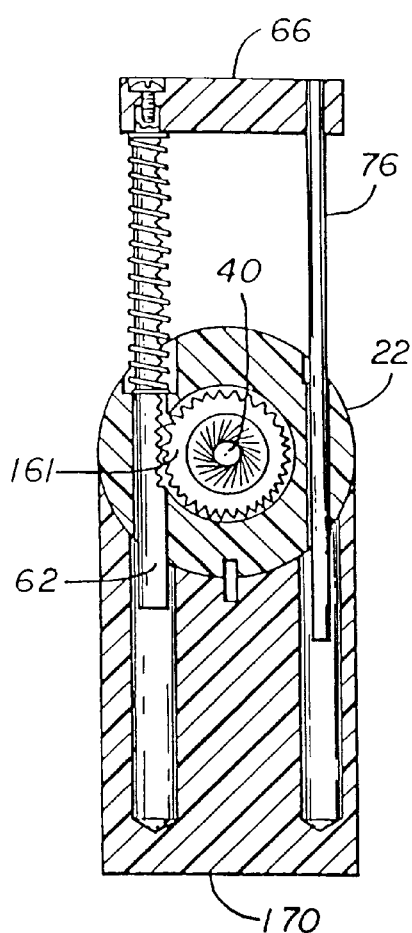
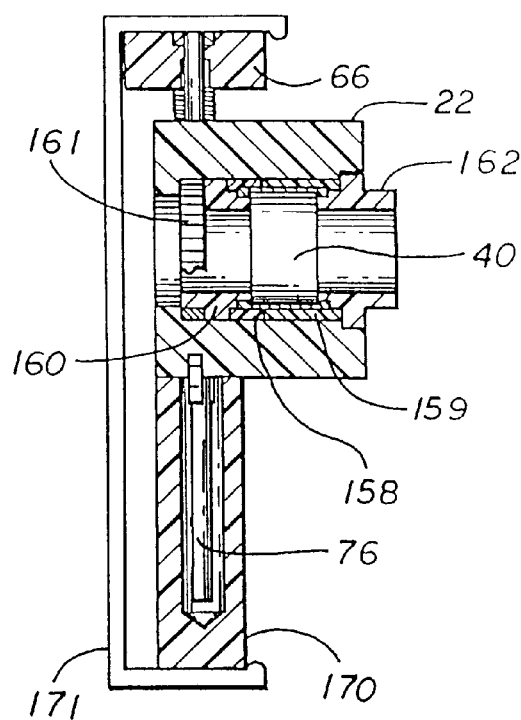
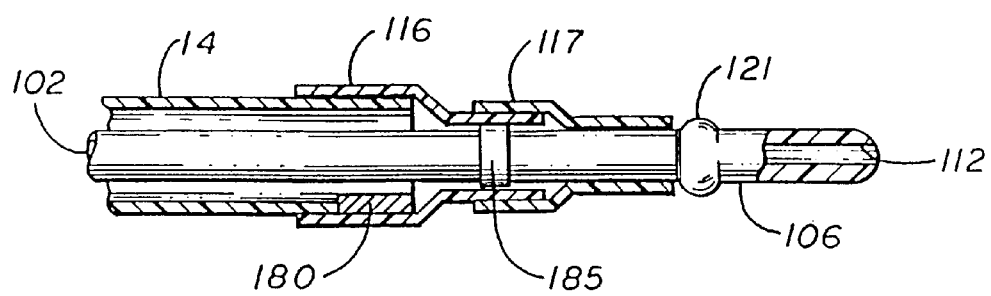
FIG. 26

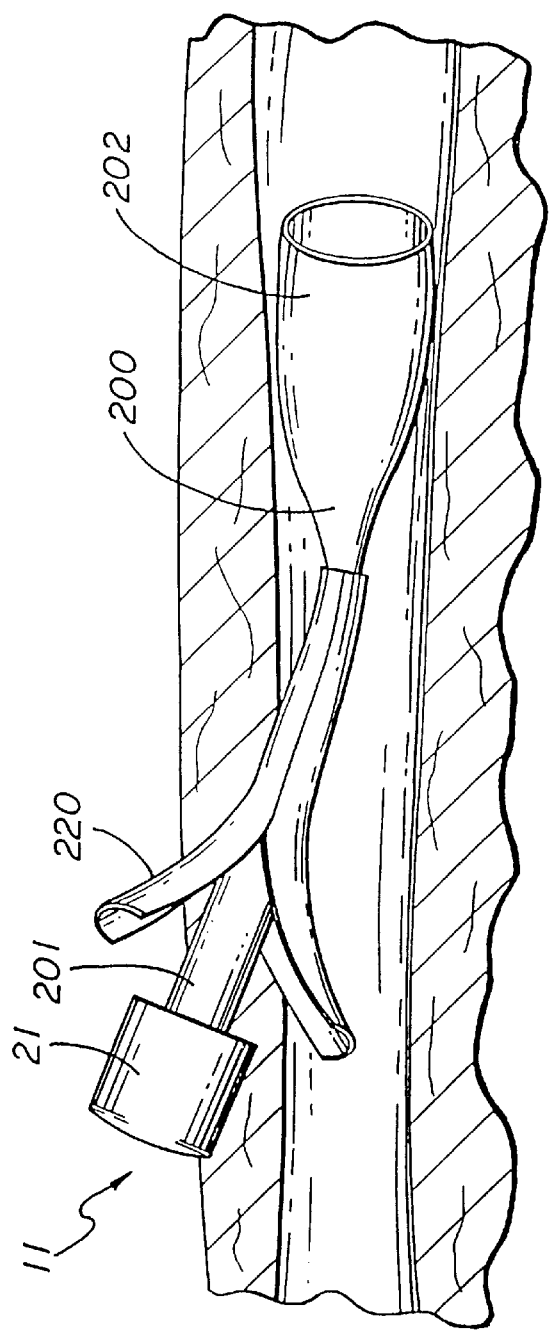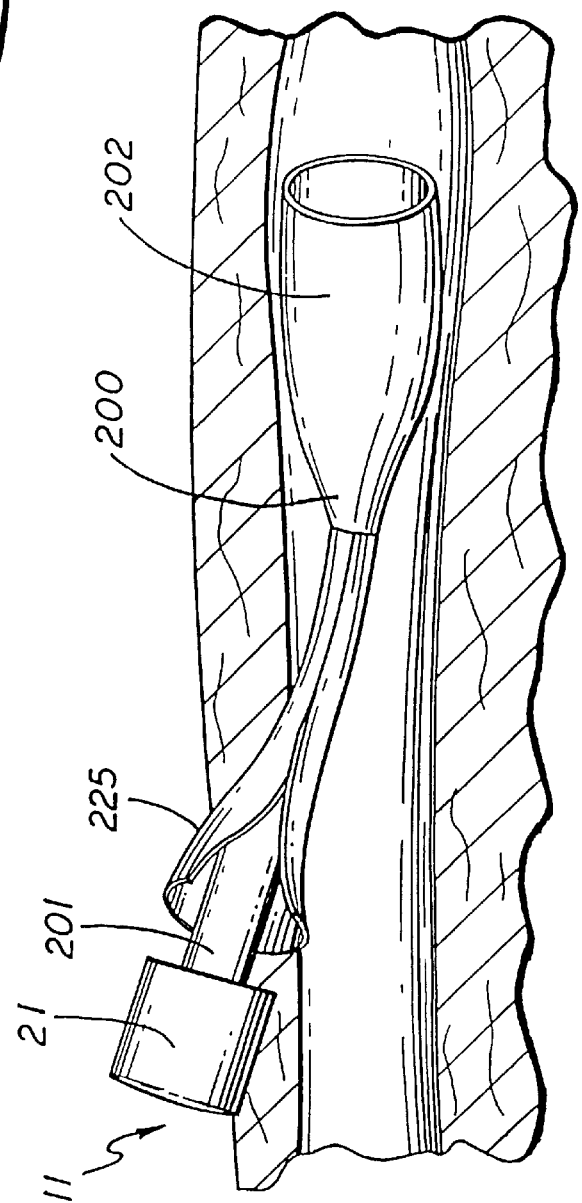

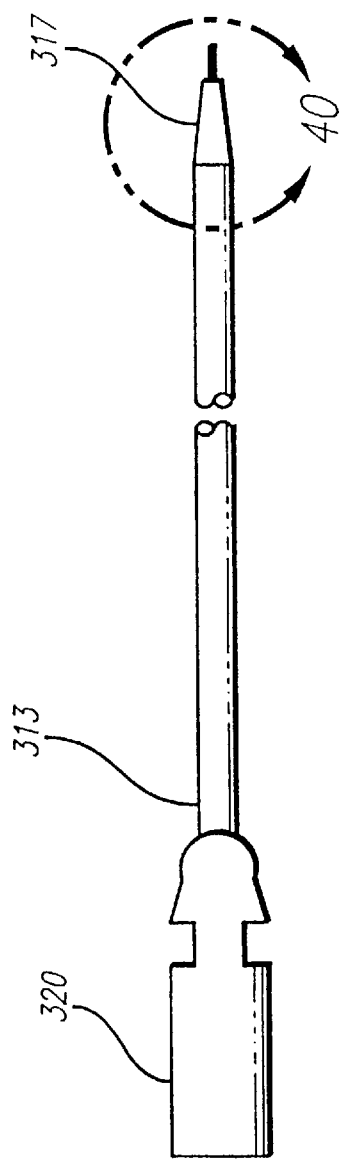
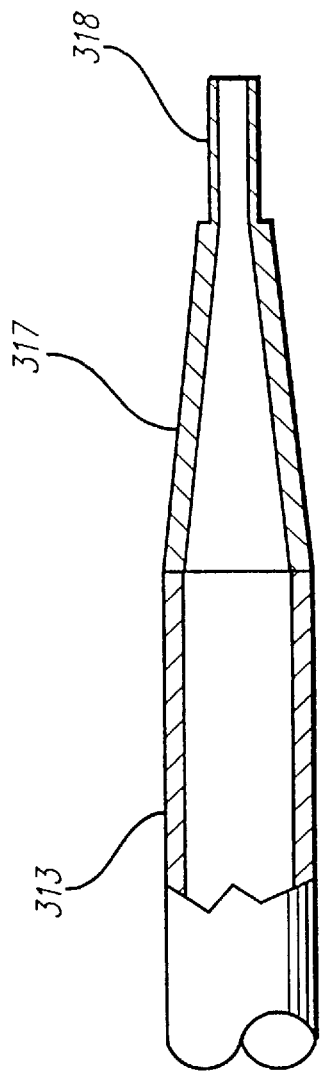
FIG. 39
FIG. 40

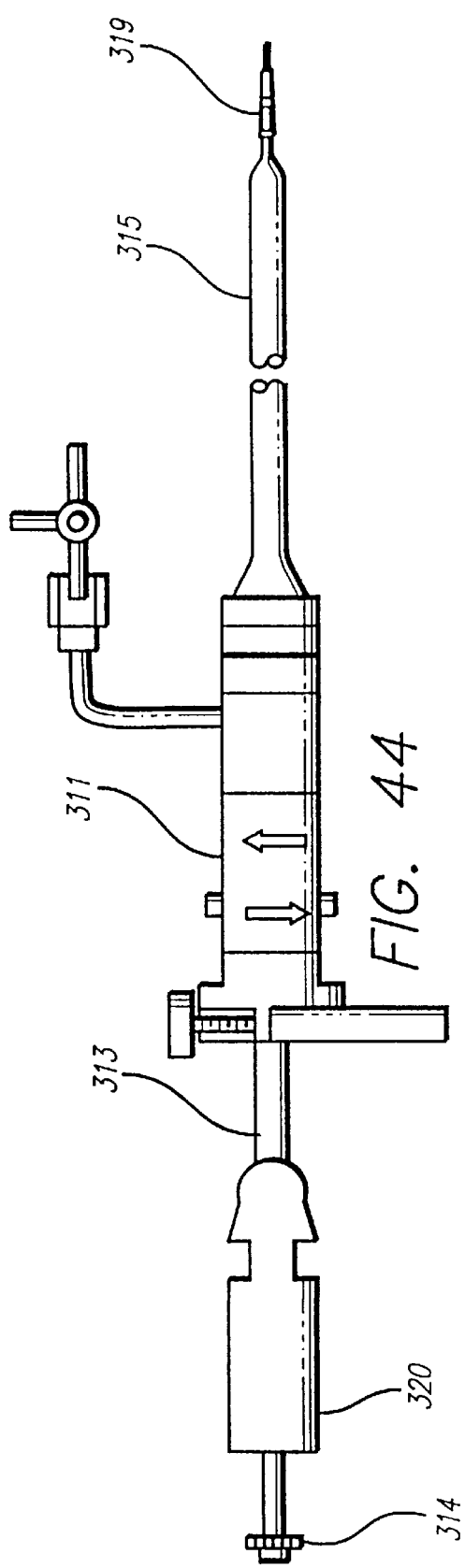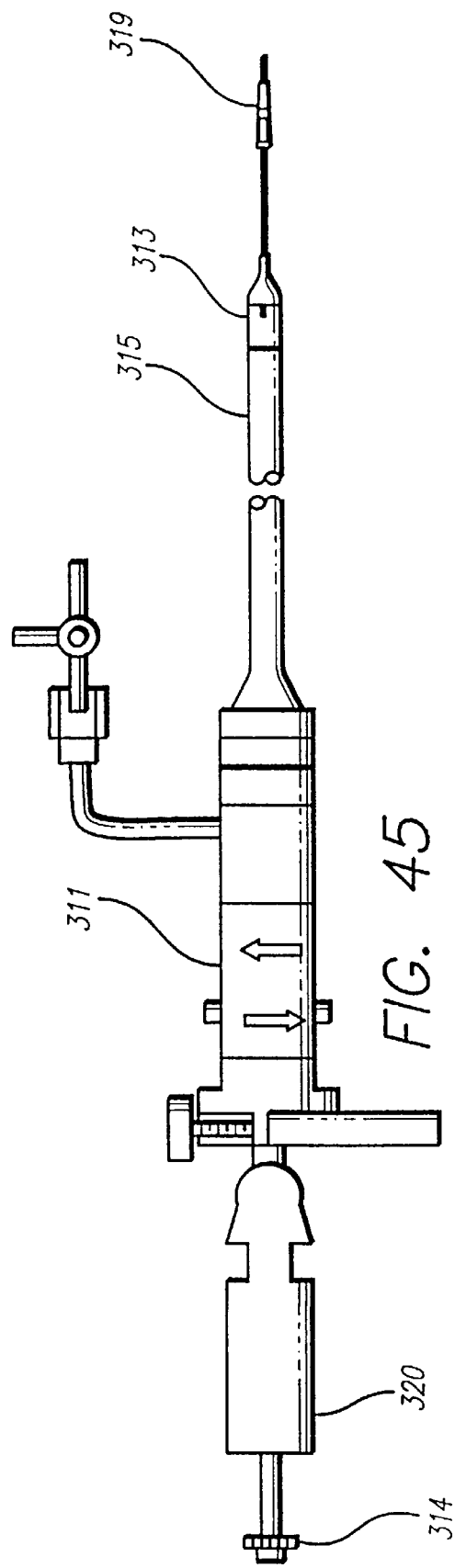

DUAL VALVE, FLEXIBLE EXPANDABLE SHEATH AND METHOD

This application is a continuation of application Ser. No. 08/905,167, filed on Aug. 1, 1997, now U.S. Pat. No. 5,935,122, which is a continuation-in-part of application Ser. No. 08/534,393, filed on Sep. 27, 1995, now U.S. Pat. No. 5,653,697, which is a continuation of application Ser. No. 08/333,229, filed on Nov. 2, 1994, now U.S. Pat. No. 5,484,418, which is a division of Ser. No. 08/109,131, filed Aug. 19, 1993, now U.S. Pat. No. 5,395,349, which is a continuation-in-part of Ser. No. 07/807,089, filed Dec. 13, 1991, now U.S. Pat. No. 5,256,150, which are hereby incorporated by reference.

BACKGROUND OF THE INVENTION

This invention relates to an expandable sheath and more particularly to a dual valve, reinforced, large-diameter expandable sheath and method of use.

Expandable access catheter assemblies have heretofore been provided to facilitate the placement and removal of diagnostic and therapeutic catheters through the vascular system. Such catheter assemblies included a flexible variable-diameter catheter body, a diameter control stylet and a flexible Y-hub. The flexible Y-hub incorporates an adjustable hemostasis valve and a side port in one branch and a diameter control stylet guide wire in another branch. A flexible variable diameter catheter body is secured to the flexible Y-hub and can be expanded between a collapsed position and an expanded position by the stylet guide wire. Several deficiencies have been found in such a device. For example, the adjustable hemostasis valve is incapable of accepting large catheters. The flexible variable-diameter catheter body is objectionable in that it has a tendency to reduce in diameter and hold onto large-diameter catheters when it is attempted to place the same through the catheter body. In addition, the tip of the stylet guide wire catches a large-diameter catheter which causes elongation of the catheter body and reduction in its diameter to grab and prevent further advancement of the large-diameter catheter. Further, the tip of the stylet guidewire may, in certain circumstances, snag the variable-diameter catheter during removal. Additional problems with existing art involve the lack of safety features to protect against operator induced inadvertent advancement of a stylet guide wire distally into the vascular system beyond a desire distance. There is therefore a need for a new and improved large-diameter expandable sheath which will overcome these deficiencies.

SUMMARY OF THE INVENTION

The present invention comprises a sheath assembly for use in introducing a catheter or other medical instrument into a corporeal vessel. The sheath assembly includes an elongate sheath tube formed of a flexible material having proximal and distal extremities and having a passage extending therethrough. The distal extremity of the sheath tube may have a reinforcing means for causing radial expansion of the distal extremity of the sheath tube to an expanded diameter.

The sheath assembly further includes a backflow adapter having a body with a central opening in fluid communication with the sheath tube. The backflow adapter includes a normally closed primary valve and may include a normally open secondary valve. When the primary and secondary valves are open they permit a medical instrument to be inserted into said sheath tube and when closed form a hemostatic seal about the instrument. The sheath assembly may further include a sheath introducer capable of being disposed in the passage of said sheath tube.

In one preferred embodiment, the sheath assembly may further include a dilator assembly for radially expanding the distal end of the sheath. The dilator assembly may have first and second coaxially oriented tubular members wherein the outer member dilates the sheath and the inner member carries a conical shaped cap at its distal end. The sheath assembly may also have a one-way locking mechanism that allows the inner tubular member to move towards the proximal end of the sheath, but restricts movement towards the distal end of the sheath.

The primary valve is disposed proximal the secondary valve. The primary valve has a cylindrical member formed of a flexible material having a proximal end and a distal end configured with a bore therein in fluid communication with the passage of the sheath tube. The primary valve also has a ring gear secured to one end of the cylindrical member, a rack for driving the ring gear to cause relative rotation between the ends of the cylindrical member to cause the cylindrical member to be twisted to close the bore extending through the cylindrical member, and biasing means for urging the rack into a position wherein the cylindrical member is rotated to a closed position.

The secondary valve is secured to the proximal extremity of the sheath tube, and has a cylindrical member formed of a flexible material having a proximal end and a distal end configured with a bore therein in registration with the passage of the sheath tube. The secondary valve includes rotating means for engaging the cylindrical member for causing relative rotation between the ends of the cylindrical member to cause the cylindrical member to be twisted to close the bore extending through the cylindrical member.

In general, it is an object of the present invention to provide an expandable sheath which can be utilized with large-diameter catheters and method for using the same. Another object of the invention is to provide a sheath of the above character which is folded longitudinally to a small diameter and which can be expanded greatly when a large-diameter catheter is to be passed through it. Another object of the invention is to provide a sheath of the above character which is provided with a backflow adapter which includes a tubular diaphragm that can be moved into an hourglass or iris-like configuration to create a fluid-tight barrier around any tubular device such as a large-diameter catheter passed through the backflow adapter and the tubular diaphragm. Another object of the invention is to provide a sheath of the above character in which a dilator can be utilized for expanding the sheath. Another object of the invention is to provide a sheath of the above character in which the backflow adaptor can be readily controlled. Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1 is a side elevational view of a large-diameter expandable sheath assembly incorporating the present invention and in which a sheath introducer is disposed in the sheath tube.

FIG. 2 is an enlarged side elevational view of the sheath introducer shown in the large-diameter expandable sheath assembly of FIG. 1.

FIG. 3 is an enlarged detail view partially in cross-section of the distal extremity of the sheath introducer shown in FIG. 2.

FIG. 4 is a cross-sectional view taken along the line 4—4 of FIG. 1.

FIG. 14 is a side elevational view of the valve or diaphragm utilized in the backflow adapter shown in FIGS. 9 and 10.

FIG. 15 is an alternative embodiment of a valve or diaphragm for use in the backflow adapter shown in FIGS. 9 and 10.

FIG. 16 is still another embodiment of a valve or diaphragm for use in the backflow adapter show in FIGS. 9 and 10.

FIG. 17 is a view similar to FIG. 9 but showing an alternative rack and pinion arrangement for the backflow adapter.

FIG. 18 is a cross-sectional view showing another embodiment of a rack for the closing and opening of the valve in the backflow adapter.

FIG. 19 is a cross-sectional view taken along the line 19—19 of FIG. 18.

FIG. 20 is a side elevational view of an alternative embodiment of the sheath assembly incorporating the present invention and in which a sheath introducer is disposed in the sheath tube.

FIG. 22 is a partial side elevational view of an alternative embodiment of an expandable sheath tube incorporating the present invention.

FIG. 23 is a cross-sectional view taken along the line 23—23 of FIG. 22.

FIG. 24 is an end elevational view looking along the line 24—24 of FIG. 21 with certain portions being shown in cross-section and with the primary valve being in a normally closed position.

FIG. 25 is a side elevational view partly in cross-section of the primary valve shown in FIG. 24 in an open position and held by a keeper.

FIG. 26 is an enlarged detailed view partially in cross-section of an alternate embodiment of the distal extremity of the sheath tube and the sheath introducer, showing the radiopaque marker band on the introducer and a radiopaque marker on the sheath tube.

FIG. 35 is a side elevational view of a sheath assembly inserted into a vessel, wherein an introducer capsule is being removed from the sheath tube.

FIG. 36 is a side elevational view of a sheath assembly inserted in a vessel wherein a removable capsule is being used to withdraw the sheath tube from the vessel.

FIG. 39 is a side elevational view of the outer tubular member of the sheath assembly of FIG. 37.

FIG. 40 is a cross-sectional view of the distal end of the outer tubular member shown in FIG. 39.

FIG. 44 is a side elevational view of the large-diameter expandable sheath assembly of FIG. 37 depicting the initial configuration of the assembly during a sheath insertion procedure into a vascular system.

FIG. 45 is a side elevational view of the embodiment of FIG. 44 showing the dilator assembly moved distally.

DESCRIPTION OF THE PREFERRED EMBODIMENTS

Figure 5:
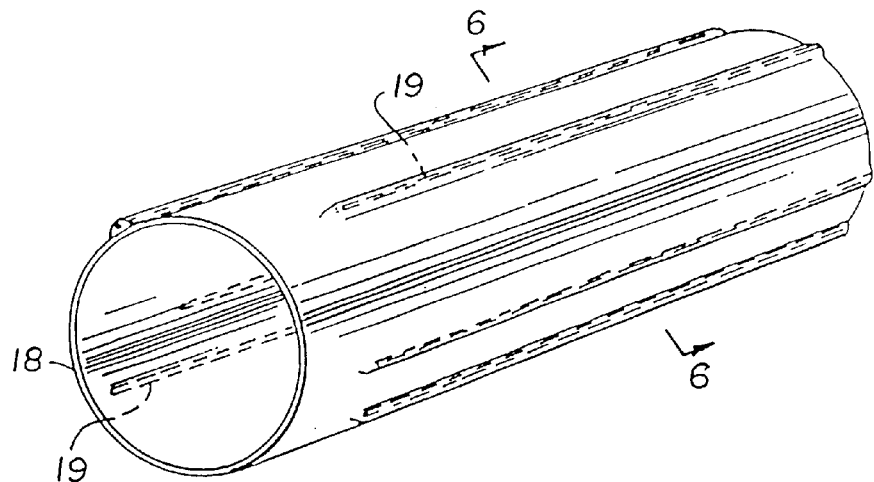
FIG. 5 is a partial side elevational view of an alternative embodiment of an expandable sheath tube incorporating the present invention.

In general, the large-diameter expandable sheath is used for introduction of a catheter into the body of a patient. It comprises an elongate sheath tube formed of a flexible material and having proximal and distal extremities and having passage therein of a predetermined maximum diameter. The distal extremity of the elongate sheath tube is folded longitudinally into a smaller diameter. A backflow adapter is secured to the proximal extremity of the elongate sheath tube. The backflow adapter has a central opening therein in registration with the passage in the sheath tube. Valve means is disposed in the central opening in the backflow adapter and is movable between open and closed positions. The valve means when in an open position permits a catheter to be introduced into the sheath and when closed forms a liquid-tight seal about the catheter extending therethrough.

More particularly as shown in FIG. 1 of the drawings, the large-diameter expandable sheath 11 consists of an elongate sheath tube 12 having proximal and distal extremities 13 and 14 and having a flow passage 16 having a maximum diameter extending therethrough. The expandable sheath 11 can have a suitable length as, for example, fifteen to thirty-five centimeters and preferably approximately eighteen centimeters with a maximum outside diameter of one centimeter. The elongate sheath tube is formed of a flexible material having a wall thickness of 0.001 to 0.020 inches (0.0254–0.51 millimeters) and preferably about 0.005 inches (0.127 millimeters) and can be formed of a suitable plastic material such as "TEFLON" (a fluorinated ethylene propylene). An alternate material is "TEFZEL" (ethylene tetrafluoroethylene). The selected material should have physical characteristics which will not be compromised by radiation sterilization.

As shown in FIG. 4, the distal extremity of the sheath tube is pleated or folded longitudinally to provide wraps or folds 17 for a distance of approximately ten centimeters from the distal end to provide a distal extremity of reduced diameter as, for example, a reduction of the outside diameter from 3/8 to 3/16 of an inch (9.52–4.76 millimeters) or approximately one-half the original size. The folding or pleating of the sheath tube 12 in this manner serves two purposes. The first purpose is to reduce the sheath diameter to facilitate introduction of the sheath and to make it less traumatic for the vessel into which it is introduced. The second reason is that with a small-diameter, thin-wall tube, as represented by the elongate sheath tube 12, there is less likelihood of kinking occurring than in a large-diameter, thin-wall tube. The distal extremity of the sheath tube 12, when folded longitudinally in this manner, serves to provide kink resistance in the distal extremity 14 while still being relatively flexible.

Figure 6:
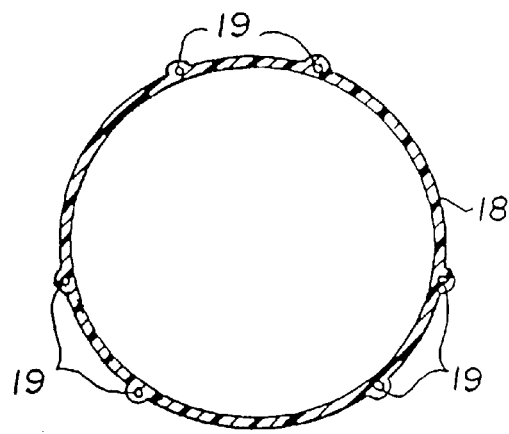
FIG. 6 is a cross-sectional view taken along the line 6—6 of FIG. 5.
Figure 7:
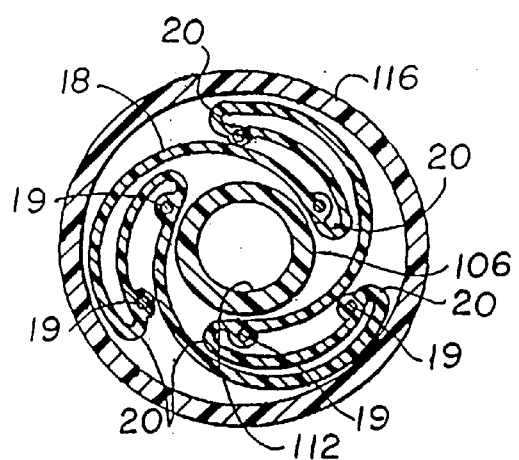
FIG. 7 is a cross-sectional view similar to FIG. 4 showing the sheath of FIGS. 5 and 6.

If it is desired to further decrease the likelihood of kinking in the large-diameter, thin-wall tube which forms the sheath tube 12, another embodiment of the sheath tube can be provided of the type shown in FIGS. 5, 6 and 7. The sheath tube 18 shown in those figures is provided with a plurality of circumferentially spaced apart flexible elongate elements 19 which are embedded in the wall of the tube 18 and extend longitudinally along the length thereof as shown in FIG. 5. The proximal extremities are offset or staggered as shown in FIG. 5 with alternate elements 19 being shorter. This offset relationship provides a gradation in stiffness in the proximal extremity of the sheath tube 18. The elongate elements 19 can be in the form of stainless steel wires having a diameter ranging from 0.005 to 0.015 inches (0.127–0.381 millimeters) and preferably a diameter of approximately 0.010 inches (0.254 millimeters). As can be seen from FIG. 6, the sheath tube 18 can bulge outwardly around the elongate elements 19 while being relatively thin between the elongate elements to retain the flexibility of the tube 18. As also can be seen from FIG. 6, the elongate elements 19 are spaced apart in the three groups to facilitate the formation of six folds 20 as shown in FIG. 7. Thus, by way of example, each set of elongate elements can have the elongate elements spaced approximately 35° apart with each set being spaced approximately 85° apart. Spacing of the elongate elements 19 in this manner facilitates the formation of the folds shown in FIG. 7. The elongate elements 19 also provide additional rigidity longitudinally of the tube 18 so as to inhibit accordioning of the tube 18 during removal of the introducer as hereinafter described.

As shown in FIG. 22, sheath tube 12 may be provided with a sheath marker 180 located at the distal end 14 of the sheath tube. The sheath marker is formed of a radiopaque alloy, for example platinum-tungsten or platinum-iridium. The sheath marker is molded inside the distal extremity of the sheath tube to enable the physician to locate the sheath tip during the operative procedure. A laminating patch is created from a tab of sheath material located at the distal tip of the sheath. This tab is folded back over and fused to the sheath tip to laminate the radio opaque marker on the inside tip of the sheath tube. Thus, the marker resides between two laminated layers of the sheath tube. As shown in FIG. 23, the distal end of the sheath tube may be folded into four bifolds 181 to form a square-like configuration, wherein the sheath marker is embedded within one of the sides 182 of the folded square.

A backflow adapter 21 is secured to the proximal extremity of the elongate sheath tube 12. The backflow adapter 21 consists of a housing or body 22 which is formed of a suitable material, for example, a plastic such as polycarbonate. The housing 22 is provided with a central bore 23 extending therethrough in axial alignment with the passage 16 of the sheath tube 12. A cylindrical sheath tube adapter 26 is disposed in the bore 23 and is provided with an annular recess 27 which receives an inwardly-extending flange 28 provided on the proximal extremity 13 of the sheath tube 12 (see FIG. 8). A tubular insert 29 formed of the same material as the sheath tube 12 but of a greater wall thickness, as for example twice the wall thickness of the sheath tube 12, is secured within an annular recess 30 in the sheath tube adapter 26 by suitable means such as an adhesive. The insert 29 serves as a reinforcement and serves to prevent collapse of the proximal extremities 13 of the sheath tube 12 when the expandable sheath 11 is used. The sheath tube adapter 26 is fixed within a first cylindrical collar 31 seated within the bore 23 and is held in place by solvent bonding the cylindrical collar 31 into the housing or body 22 to prevent longitudinal and/or rotational movement of the first collar 31 relative to the housing or body 22. A second collar 34 is also seated in the bore 23 and is rotatable therein. An annular ring gear 36 having teeth 36 thereon is also rotatably mounted in the bore 23 as hereinafter described.

A cylindrical or tubular valve member or diaphragm 40 is disposed between the first and second collars 31 and 34, and is provided with a bore or flow passage 41 extending therethrough. The valve member 40 is provided with inwardly extending annular lips or flanges 42 and 43 provided on opposite extremities of the same (see FIGS. 8 and 14). The flange 43 is seated in an annular recess 46 in the sheath tube adapter 26 and is retained therein by the first collar 31. The flange 42 is seated in an annular recess 47 provided in a retaining ring 48 and retained therein by the second collar 34. An annular protrusion 49 is formed integral with the retaining ring 48 and engages one side of the toothed ring gear 37 which is secured to the retaining ring 48 by suitable means such as an adhesive. Similarly, the retaining ring 48 functionally engages the second collar 34 and causes the second collar 34 to rotate therewith.

The diaphragm or valve member 40 can have a suitable size as, for example, a length of 0.3 to 0.45 inches (7.62–11.43 millimeters) and preferably a length of approximately 0.3 inches (7.62 millimeters), and an inside diameter of 0.35 to 0.5 inches (8.89–12.7 millimeters), and preferably an inside diameter of 0.375 inches (9.52 millimeters), with a wall thickness ranging from 0.005 to 0.015 inches (0.127–0.381 millimeters), and preferably a wall thickness of 0.007 inches (0.178 millimeters). The annular lips 42 and 43 can extend inwardly for a distance of 0.032 inches (0.813 millimeters) from the outer wall surface and have a length of approximately 0.050 inches (1.27 millimeters). The diaphragm or valve member 40 can be formed of a suitable material, such as a silicone elastomer, as, for example, Dow "SILASTIC" 97-4720. It can have a Shore A hardness ranging from 20–80 and preferably a Shore hardness of 40 A. Alternatively, a low durometer, tear-resistant rubber-like latex material can be utilized.

Other diaphragm or valve members such as shown in FIGS. 15 and 16 can be utilized which have the same physical conformation. In the embodiment shown in FIG. 15, small denier polyester fibers 52 are bonded to the exterior surface of the diaphragm 51 with a silicone adhesive so that the fibers 52 extend circumferentially around the outside surface of the diaphragm 51. Such fibers serve to impede radial and longitudinal distention of the diaphragm or valve member 51. The diaphragm or valve member 56 shown in FIG. 16 is provided with a cylindrical wall 57 which increases in thickness in a direction towards the distal extremity of the diaphragm. This helps the diaphragm to withstand the pressures applied to the diaphragm during use, which may cause the diaphragm to distend and leak.

Means is provided for causing relative rotation between the sheath tube adapter 26 and the retaining ring 48 for opening and closing the bore or flow passage 41 by twisting of the cylindrical valve member or diaphragm 40. This is accomplished by fixing the first collar 31 and the sheath tube adapter 26 within the housing or body 22 by suitable means such as solvent bonding and causing rotation of the retaining ring 48 by the use of a rack 61. The rack 61 consists of a rod 62 formed of a suitable material such as stainless steel which extends through a hole 63 (see FIG. 11) in the housing or body 22 in a direction which is tangential of the bore 23. The rod 62 is disposed immediately adjacent a flange 64 formed in the body 22 against which the ring gear 36 rotates. The hole 63 opens into the bore 23 so that rack teeth 64 provided on the one side of the rod 62 engage the toothed ring gear 36 whereby upon reciprocatory movement of the rack 61, the ring gear 36 is rotated through an angle ranging from 180° to 360°, and preferably an angle of at least 270°.

Figure 12:
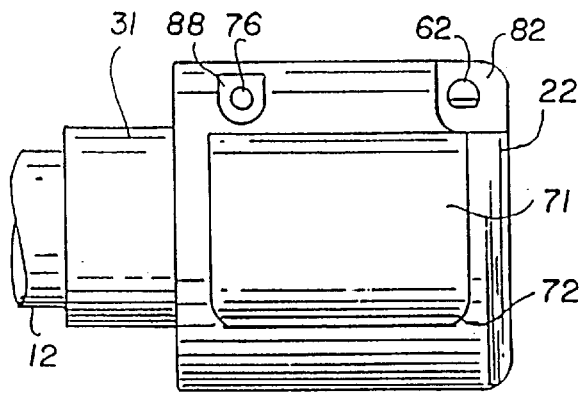
FIG. 12 is a bottom plan view looking along the line 12—12 of FIG. 11.
Figure 13:
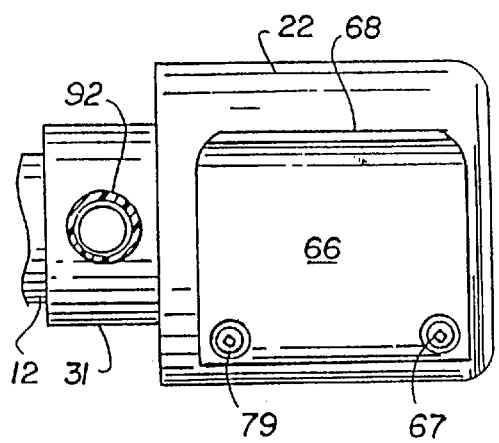
FIG. 13 is a top plan view looking along the line 13—13 of FIG. 11.

An actuator 66 formed of a suitable material such as plastic is mounted on the upper extremity of the rod 62 and is secured thereto by suitable means such as an Allen-head screw 67 set into the rod 62, as shown in FIG. 13. The actuator 66 is generally rectangular in plan and is provided with an upstanding lip 68 so that it conforms to the confor-mation of the index finger of the hand which is to be utilized for actuating the rack 61. The actuator 66 is provided with a reinforcing rib 69 along one edge of the same. A similar actuator member 71 is provided on the body 22 underlying the actuator 66 and is also provided with a downwardly extending lip 72. The actuator member 71 is secured to the body 22 by suitable means such as an adhesive. The member 71 also has a rectangular configuration in plan and is sized so that it is adapted to be engaged by the thumb of the hand, as shown in FIG. 12. Thus, one hand can be utilized for operating the backflow adapter 21 by the index finger of the hand grasping the actuator 66 and the thumb of the same hand grasping the member 71.

A stabilization and guide rod 76 extends through a tangential bore 77 (see FIG. 11) provided in the body 22 which is spaced apart from the bore 63 and extends in a direction which is parallel thereto. The rod 76 is formed of a material such as stainless steel and is provided with a collar 78 which extends through the reinforcing rib 69 of the actuator 66 and is secured therein by suitable means such as an Allen-head screw 79.

In an alternative embodiment of the normally closed primary valve if shown in FIGS. 24 and 25, the actuator 66 is turned 900 so that guide or stabilizer rod 76 is positioned on the opposite side of the proximal valve housing 22 to the rack 62. A ring gear 161 is configured into a gear hub 160 which causes rotation of proximal diaphragm retaining ring 158. The distal end of the primary diaphragm 40 is secured to the distal retaining ring 159 which is fixed relative to the proximal valve housing and is positioned proximal a distal retaining hub 162. The primary diaphragm is opened by depressing the actuator which causes the rack to move the ring gear and rotate the gear hub and proximal retaining ring. In addition, a cover 170 is added to the bottom of the body to encase the bottom portions of the rack and stabilizer rod. Also, a "C"-shaped keeper 171 can be used to maintain the actuator in the compressed or open valve position by placing one end over the actuator and the other end over bottom of the cover.

Figure 9:
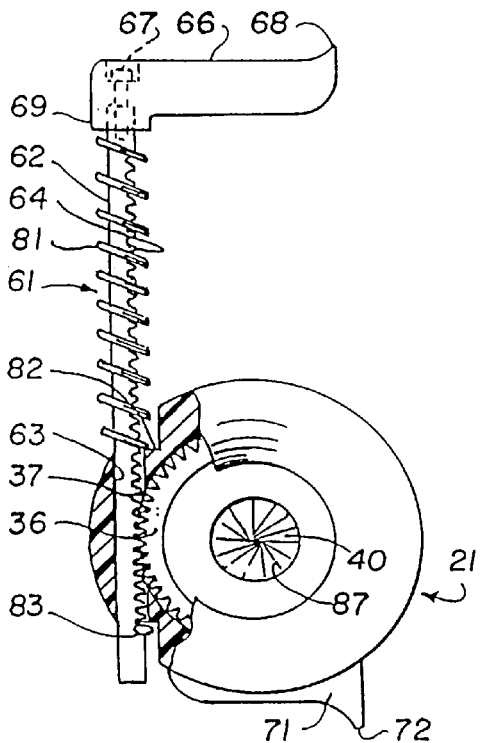
FIG. 9 is an end elevational view looking along the line 9—9 of FIG. 8 with certain portions being shown in cross-section and with the valve carried by the backflow adapter being in a normally closed position.
Figure 10:
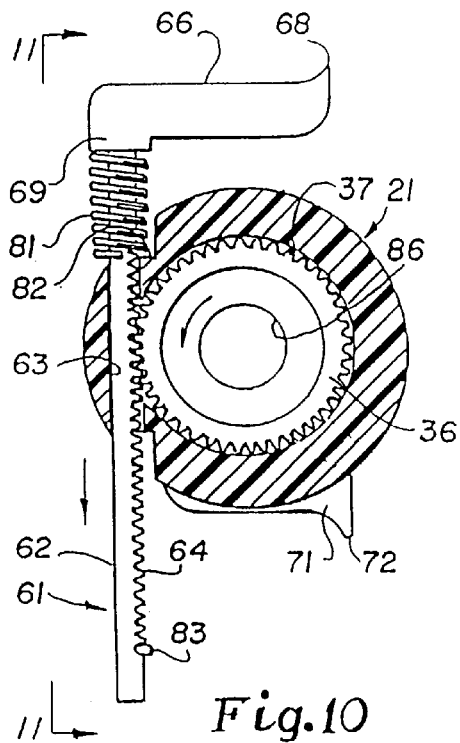
FIG. 10 is a view similar to FIG. 9, but showing the valve in an open position.
Figure 11:
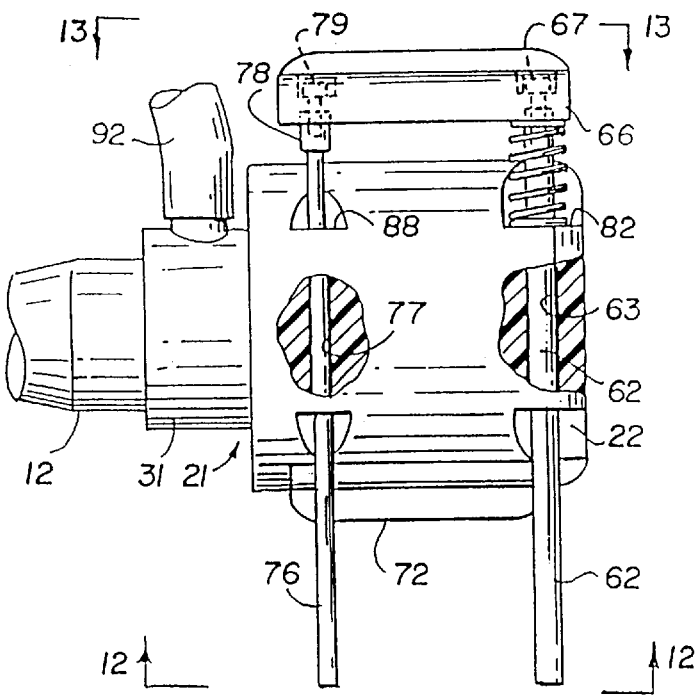
FIG. 11 is a side elevational view partially in cross section opposite the side shown in FIG. 8 of the proximal extremity of the expandable sheath.

Referring to FIG. 11, means is provided for yieldably returning the rack 61 into a position so that the valve member or diaphragm 40 is in a normally closed position and consists of a coil spring 81 coaxially mounted on the rod 62 and having one end engaging the actuator 66 and having the other end engaging a seat 82 provided in the body 22. Means is provided for preventing the spring 81 from urging the rod 62 out of the bore 63 and consists of a lump 83 of solder or a braising material provided on the rod 62 adjacent the lower extremity of the rack teeth 64. Thus, it can be seen by the hand engaging the backflow adapter 21 using the index finger to engage the actuator 66 and the thumb to engage the actuator member 71, the rack 61 can be reciprocated back and forth to open and close a bore 86 extending through the retaining ring 48 and the sheath tube adapter 26 by forming an hourglass or iris-like closure as shown in FIG. 9 in which the radially extending lines 87 shown represents the folding over of the elastomeric material of the valve member or diaphragm 40. The collar 78 provided on the stabilization rod 76 serves to stop further travel up the rack when the collar 78 engage a seat 88 provided in the body 22. In this position, the spring 81 is almost completely compressed as shown in FIG. 10. Following the release of the actuator 66, the spring 81 returns the rack 62 to its home position and causes the valve member or diaphragm 40 to be completely closed as shown in FIG. 9.

The ring gear 36 can be formed of a suitable material such as stainless steel and can have any suitable number of teeth.

Alternatively, the ring gear can be formed of a suitable plastic such as nylon. The other portions of the backflow adapter 21 as, for example, the body 22, the first collar 31, the second collar 34, the retaining ring 48 can be formed of a suitable plastic such as polycarbonate. The metal parts such as the rod 62, the stabilization rod 76 and the spring 81 can be formed of a suitable material such as stainless steel.

Figure 8:
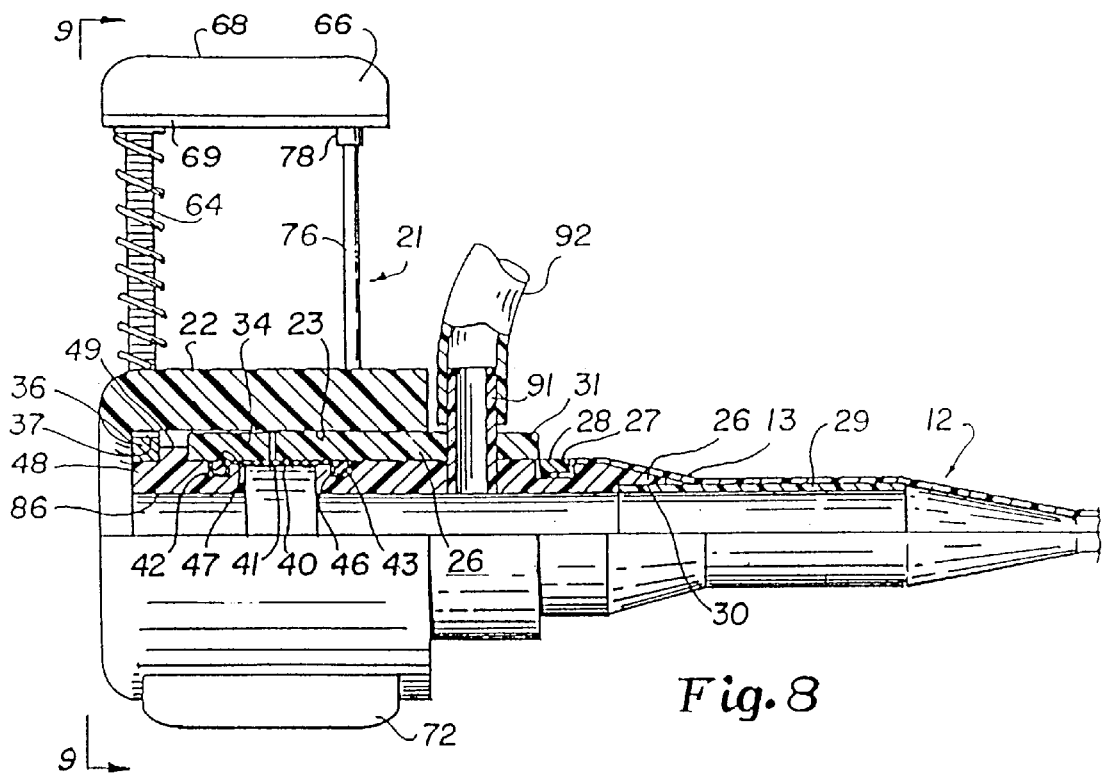
FIG. 8 is an enlarged side elevational view partially in cross-section of the proximal extremity of the large expandable sheath of the sheath assembly shown in FIG. 1 and particularly showing the backflow adapter.

As shown in FIGS. 1 and 8, means is provided for introducing liquid as, for example, a radiopaque liquid, into the bore 86 and consists of a tube 91 formed of a suitable material such as plastic extending through the first collar 31 and through the sheath tube adapter 26 so that it is in communication with the bore 86. Flexible tubing 92 is connected to the tube 91 and has a stopcock 93 of a conventional type mounted thereon which is provided with a Luer-type fitting 94. The stopcock 93 is provided with a knob 96 which can be utilized for moving the stopcock 93 between open and closed positions.

Figure 21:
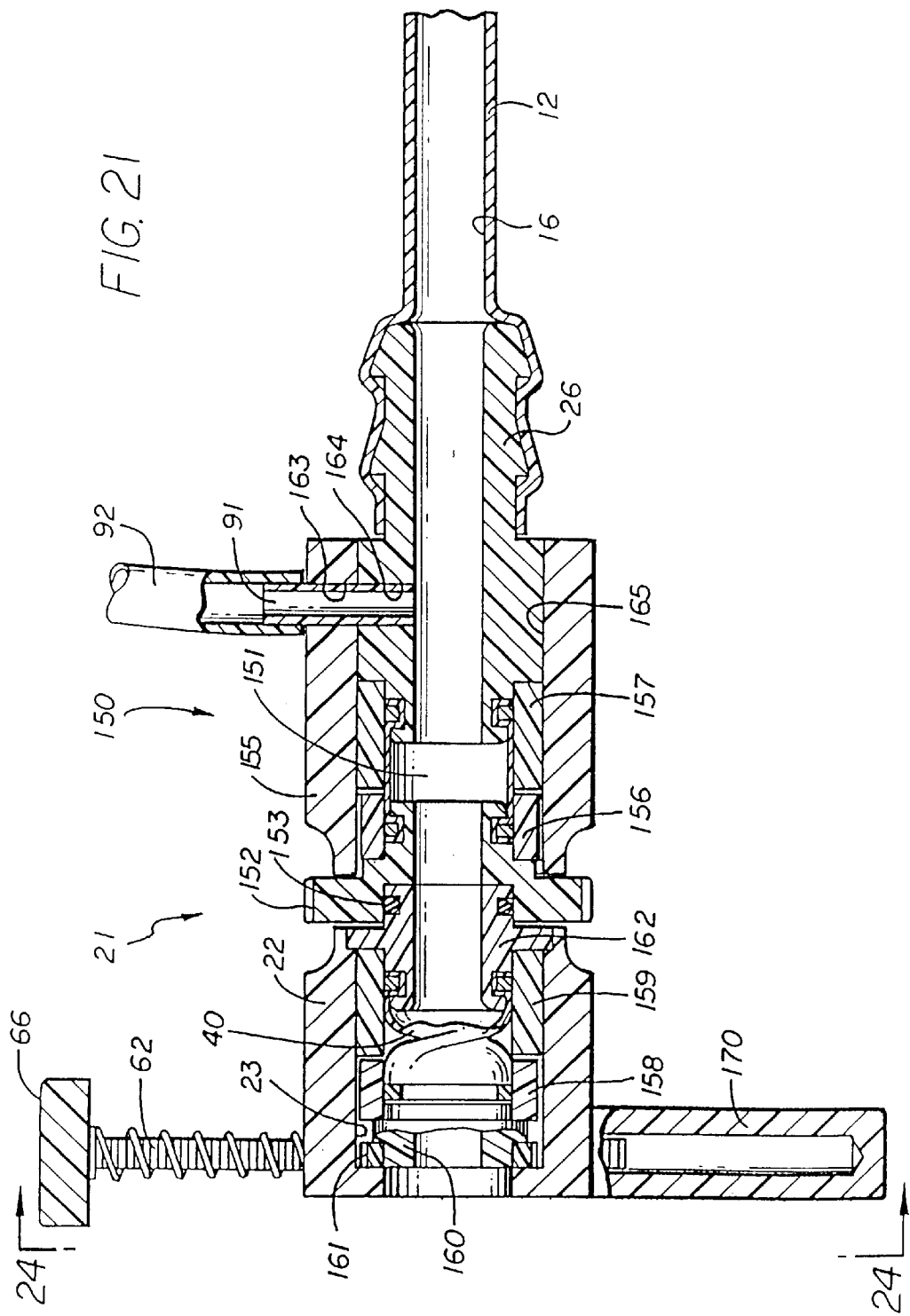
FIG. 21 is an enlarged elevational view partially in cross-section of the proximal extremity of the sheath assembly shown in FIG. 20 and particularly showing the back-flow adapter.

As shown in FIGS. 20–21, an alternate embodiment of the sheath assembly 11 includes a normally open secondary valve assembly 150 located adjacent the primary valve housing 22 of the backflow adapter 21. The secondary valve assembly contains a secondary diagram 151 which operates substantially the same as the primary diaphragm 40 and is actuated by a thumb wheel 152. The secondary diaphragm is made of silicone and is constructed substantially the same as the primary diaphragm. The secondary diaphragm is configured to have a suitable length, diameter and wall thickness to be compatible with the primary diaphragm. Similarly, each of the materials used in the secondary valve assembly for constructing and mounting the secondary diaphragm are substantially the same as the materials previously described for the backflow adapter assembly.

The primary valve assembly is configured similar to that described above in conjunction with FIGS. 24 and 25. Secondary valve housing 155 is provided with a central bore 165 which is in fluid communication with the central bore 23 of the primary valve housing 22 and the passage 16 of the sheath tube 12. Likewise, secondary diaphragm or valve member 151 is provided with a flow passage extending therethrough. Thus, an instrument such as the sheath introducer 101 may be passed through the primary diaphragm when the secondary diaphragm is closed, thereby preventing blood flow through the proximal end of the large-diameter expandable sheath assembly 11. Also, orifice 163 in the valve housing and orifice 164 in the sheath tube adapter 26 are provided to accept tube 91 connected to the flexible tubing 92 of a introducer sideport assembly (not shown).

As shown in FIG. 21, the secondary valve assembly 150 comprises a secondary valve housing 155 which contains secondary diaphragm 151 and thumb wheel 152. The proximal end of the secondary diaphragm is secured to the thumb wheel by proximal retaining ring 156. The distal end of the secondary diaphragm is fixed relative to the secondary valve housing by distal retaining ring 157. Rotation of the diaphragm is achieved by rotating the thumb wheel so as to cause motion to only the proximal end of the secondary diaphragm. A rotational stop (not shown) is positioned on the thumb wheel to prevent excess rotation of the secondary diaphragm. The rotational stop may be comprised of two $\frac{1}{32}$ of an inch (0.79 millimeters) dowel pins located on the thumb wheel and the secondary valve housing which are configured to engage each other to limit the rotation of the thumb wheel. Additionally, a silicone o-ring 153 positioned proximate the thumb wheel in the primary diaphragm distal retaining hub 162 allows rotation of the thumb wheel while preventing fluid from leaking from the backflow adapter housing.

A sheath introducer 101 is provided as a part of the assembly shown in FIG. 1 and as shown in FIG. 2 consists of an elongate tubular member 102 formed in three sections 103, 104 and 106 of different diameters. The elongate tubular member 102 can be formed of a suitable plastic material such as "PEBAX" which is formed of polyether Block Amides which is loaded with approximately 10% barium sulfate to make the same visible under X-rays. Section 103 can have a diameter ranging from 0.15 to 0.3 inches (3.81–7.62 millimeters) and preferably an outside diameter of $\frac{3}{16}$ of an inch (4.75 millimeters). The section 104 can have a suitable diameter as, for example, 0.08 to 0.15 inches (2.03–3.81 millimeters) and preferably a diameter of $\frac{1}{8}$ of an inch (3.17 millimeters). The section 106 can have a diameter ranging from 0.06 to 0.12 inches (1.52–3.05 millimeters) and preferably a diameter of 0.08 inches (2.03 millimeters). The distal extremities of the sections 103 and 104 are provided with tapers 107 and 108, respectively, so as to provide a tapered transition from one diameter to another. A Luer-type fitting 111 is mounted on the proximal extremity of the tubular section 103. A bore or lumen 112 (see FIG. 4) of a suitable size as, for example, one capable of passing a 0.038 inches (0.97 millimeters) guidewire, is provided in the section 106 as well as in the sections 104 and 103 extending the length of the tubular member 102.

As shown in FIG. 3, a tube 116 is mounted on the distal extremity 106 of the sheath introducer 101 and is formed of a suitable material such as silicone and is retained thereon in a suitable matter by the use of polyethylene shrink tubing 117. A cylindrical enlargement or annular bump 121 is provided on the tubular section 106 adjacent the distal extremity of the shrink tubing 117 and serves to prevent the sleeve 116 and the shrink tubing 117 from accidentally slipping off of the distal extremity of the tubular section 106.

When the sheath introducer 101 is disposed in the expandable sheath 11, as shown in FIG. 1, the proximal extremity of the silicone sleeve 116 is disposed over the distal extremity of the sheath tube 12 and serves to prevent the sharp edges of the folded sheath tube 12 from causing trauma to the interior wall of a vessel when it is introduced into the vessel when the sheath is introduced as hereinafter described. A vent hole 123 is provided in the sheath introducer 101 which is in communication with the passage 112 proximal of the silicone sleeve 116, as shown in FIG. 3. The vent hole 123 can be utilized for flushing the elongate sheath tube 12 through the side port fitting 94 prior to use of the expandable sheath in a surgical procedure.

As shown in FIG. 26, a radiopaque marker band 185 may be positioned proximal to distal end of the sheath introducer 101. The marker band is made of a radiopaque alloy, platinum-tungsten or platinum-iridium. The marker band is positioned just proximal the retaining bump 121 over the elongate tubular member 102 and within silicone sleeve 116 and polyethylene shrink tubing 117. The platinum alloy band is held in place by both the silicone sleeve and the polyethylene shrink tubing. As appropriate, the marker band may be positioned elsewhere along the length of the sheath introducer, such as within the most distal tubular section 106.

Operation and use of the expandable sheath 11 in conjunction with the sheath introducer 101 may now be briefly described as follows. Let it be assumed that the patient has been prepared in a conventional manner and that it is desired to enter a peripheral vessel such as an artery or a vein of the patient. The desired vessel is exposed and a longitudinal or transverse incision made into that vessel. A guidewire of a suitable size is then selected as, for example, a guidewire having a diameter of 0.038 inches (0.97 millimeters). The guidewire (not shown) is introduced into the vessel and then the expandable sheath assembly 11 shown in FIG. 1 is placed over the guidewire by placing the proximal extremity of the guidewire into the lumen 112 provided in the elongate tubular member 102 and advanced through the Luer fitting 111. The rounded tip and the small diameter of the section 106 of the tubular member 102 facilitate advancement of the sheath introducer 101 into the vessel without traumatizing the vessel. The small-diameter tip section 106 is followed by the elongate sheath tube 12 which has been collapsed as hereinbefore described about the tubular section 106 until the sheath tube 12 has been introduced to the proper depth in the vessel. As soon as the sheath tube 12 has been positioned in the vessel, the sheath introducer 101 is advanced relative to the elongate sheath tube 12 by using one hand to hold the backflow adapter 21 which is connected to the sheath tube 12 and the other hand to push the sheath introducer 101 so that the proximal extremity of the silicone sleeve 116 moves off of the distal extremity of the sheath tube 12 to expose the same.

As soon as this has been accomplished, the sheath introducer 101 is pushed forward so that section 103 enters the collapsed section of the sheath tube 12 to commence opening of the same. The sheath introducer 101 is then removed through the backflow adapter 21. The sheath introducer can be removed by grasping the backflow adapter 21 by the fingers of the hand as hereinafter described to at least partially open the same to permit removal of the sheath introducer and dilator 101 while minimizing the flow of blood from the sheath tube 12. The backflow adapter can then be released. The sheath 11 and its backflow adapter is now in its normally closed state to provide a hemostatic seal closing the flow passage 86.

The physician conducting the procedure then selects the desired catheter or other device which is desired to be introduced through the expandable sheath 11. Such a device should have a diameter of 8.5 millimeters or less or which is at least slightly less than the diameter of the bore 86. The physician grasps the actuator members 66 and 71 and presses the same to operate the rack 61 to open the diaphragm or valve member 40 permitting the physician to insert the device as, for example, the catheter through the expandable sheath 11. As soon as the catheter has been advanced as far as desired, the physician releases the pressure on the actuator members 66 and 71 permitting the diaphragm 40 to close around the device as, for example, the catheter inserted through to form a hemostatic seal about the catheter. If it is desired to reposition the catheter, it is merely necessary to push or pull the catheter and it will slide freely through the diaphragm. When it is desired to remove the catheter, the catheter need only be pulled out of the sheath 101 and the diaphragm will seal closed forming a hemostatic seal.

A silicone coating may be applied to the pleated sheath tube 12. Coating may be applied to the inner and outer surfaces prior to attachment to the backflow adapter 21. The silicone coating on the inside diameter of the sheath tube reduces the amount of force required to advance catheters and the like through the sheath tube. Additionally, the silicone coating on the outside of the sheath tube may reduce the amount of force required to advance the expandable sheath 11 into a vessel. A suitable silicone coating material is "HYDRO-SIL-D 1.0" available from TUA systems of Sarasota, Fla. Additionally, a silicone lubricant may be applied to the ring gear 36 on the primary valve assembly and the adjacent to bearing surfaces.

The method for introducing a medical instrument into the body of a patient using the dual valve expandable sheath assembly 11 shown in FIGS. 21–26 involves opening the valves to minimize blood flow through the sheath assembly 11. First, the sheath introducer 101 is placed within the sheath assembly such that the distal end 14 of the sheath tube 12 resides in the introducer sleeve 116, as shown in FIG. 26. This step may be performed as part of the manufacturing process. After the patient is prepared for the procedure, the sheath tube and the sheath introducer are intraluminally inserted into the patient, usually through a cutdown in a vessel such as a femoral artery. The distal end 106 of the sheath introducer is then inserted into the vessel until the distal end of the sheath tube is within the vessel. The sheath introducer is then advanced into the vessel relative to the sheath tube, allowing the distal end of the sheath tube to expand. In addition, the sheath introducer may be further advanced into the sheath assembly to dilate the distal end of the sheath tube.

Next, the sheath introducer 101 is removed from the sheath assembly 11. As the distal end 106 of the sheath introducer is removed from the sheath tube 12, the secondary valve 151 is closed to form a substantially fluid tight seal between the passage 16 in the sheath tube and the secondary valve assembly 150. After the secondary diaphragm 151 is closed, the primary diaphragm 40 may be opened to fully remove the sheath introducer. Then the distal end of a catheter or other medical instrument may be inserted through the primary valve. The primary diaphragm is then closed to form a substantially fluid tight seal around the medical instrument. Next, the secondary diaphragm is opened to allow the distal end of the medical instrument to be inserted through the secondary valve assembly, through the passage in the sheath tube and into the vessel of the patient. After the procedure has been completed, the medical instrument and the sheath assembly can be removed from the vessel and the incision which has been made in the vessel for permitting passage of the sheath assembly can be sutured.

It can be seen from the foregoing that there has been provided an expandable sheath 11 which can be made in various sizes to accommodate large-diameter devices while still providing the desired hemostatic seal. The expandable sheath can be readily inserted and removed. The sheath introducer 101 facilitates this introduction. It is provided with a distal extremity 106 which is small in diameter to permit the sheath tube 12 to be wrapped about the same as hereinbefore described. The sheath introducer 101 is provided with sections 103 and 104 of larger diameters to provide additional rigidity to the sheath introducer 101 to facilitate pushing of the sheath introducer when introducing the expandable sheath 11 into the vessel of the patient.

An alternative mechanism for actuating the diaphragm 40 is shown in FIG. 17 and consists of a pinion 131 which engages the ring gear 36 and is disposed in a cylindrical recess 132 provided in the body 22. The pinion 131 is mounted on a shaft 133. Another gear 134 is mounted on the shaft 133 and has a smaller diameter than the diameter of the pinion 131 and engages the rack teeth 64 provided on the rod 62. By providing such a gear arrangement, it can be seen that it is possible to provide a shorter rack to achieve the same degree of ring gear rotation for opening and closing of the diaphragm 40.

As can be seen in FIGS. 18 and 19, there is shown another embodiment of a mechanism for actuating the diaphragm 40. As shown therein it consists of a flexible rack 141 that is comprised of a flexible member 142 which is provided with rack teeth 143 on one side of the same which are adaptable to engage the ring gear 36. The member 142 extends through a semicircular slot 144 provided in the body so that it extends through the body and around the ring gear 36. An actuator 146 is provided formed integral with the rack 141 for operating the rack 141 with the fingers of the hand. In this construction the rack is substantially contained within the body 22.

As shown in FIGS. 27–36, the expandable sheath 11 may include a reinforced sheath tube 200. The reinforced sheath tube is similar to the elongate sheath tube 12 and similarly has proximal and distal extremities 201 and 202. A flow passage 203 is provided having a maximum diameter extending therethrough. One suitable material for the reinforced sheath is in an expanded PTFE (polytetrafluoroethylene). Such materials may be obtained from Impra of Temp, Ariz. and W. L. Gore of Flagstaff, Ariz. An example of a suitable size for a sheath tube for use with large catheter systems would include an outer diameter of approximately 0.345 inches (8.76 millimeters) with a wall thickness of 0.005 inches (0.127 millimeters) and having a length of about twenty centimeters.

Figure 27:
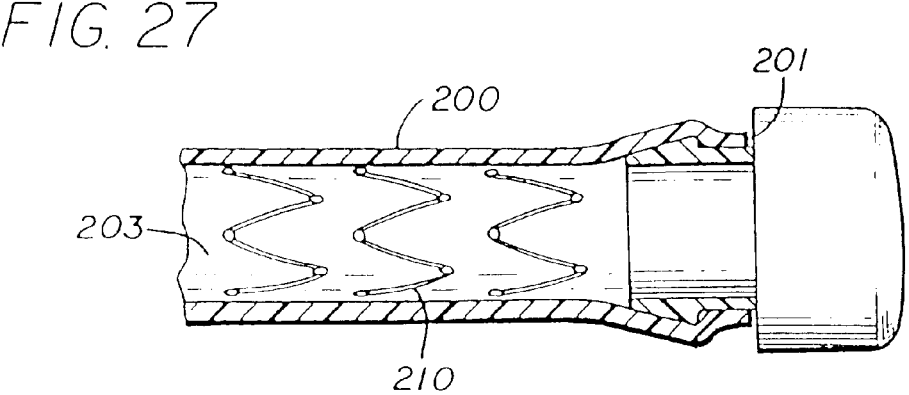
FIG. 27 is a partial side elevational view in cross-section of an alternate embodiment of an expandable sheath tube incorporating a self-expanding reinforcement means.
Figure 28:
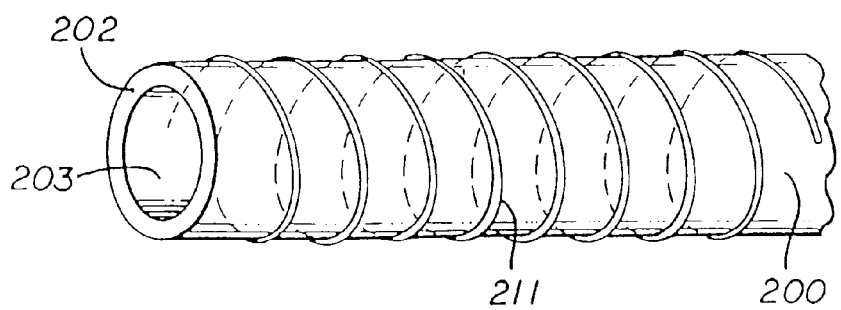
FIG. 28 is a partial side elevational view of an alternate embodiment of an expandable sheath tube incorporating a helical coil.
Figure 29:
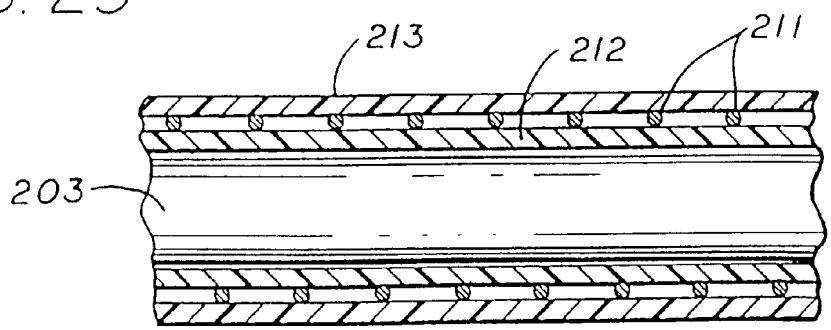
FIG. 29 is a partial side elevational view in cross-section of an alternate embodiment of an expandable sheath tube incorporating a helical coil embedded between an inner sheath tube and an outer sheath tube.
Figure 30:
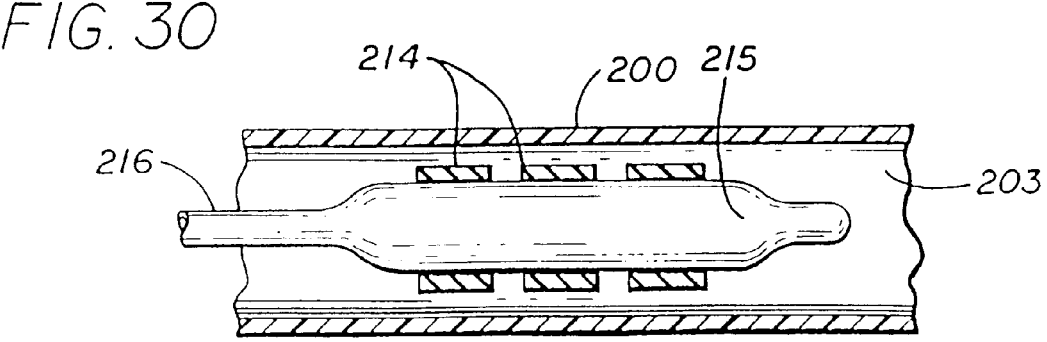
FIG. 30 is a partial side elevational view in cross-section of an alternate embodiment of an expandable sheath tube incorporating stents and a balloon for expanding the stents.

The reinforced sheath tube 200 could be supported by stents, coiled wire, coiled plastic or similar means. As shown in FIG. 27, a series of self-expanding supports 210 may be placed within the sheath tube for radial expansion. Similarly, as shown in FIG. 28, a coil 211 may be attached to the outside of the sheath tube to allow for self-expansion. Alternatively, the coil support may be embedded within an inner sheath tube 212 and outer sheath tube 213, as shown in FIG. 29. The coil or expansion system may be made of a 0.012 inches (0.3 millimeters) nitinol or similar alloy wire. As shown in FIG. 30, the reinforced sheath may include balloon expandable stents 214 which may be expanded by a balloon 215 and catheter 216 or similar means.

Figure 31:
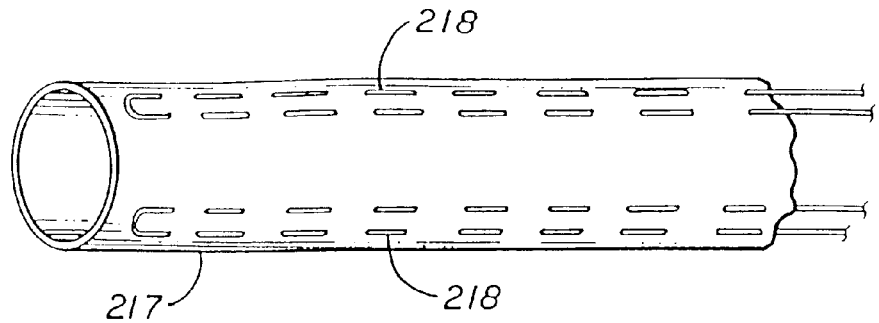
FIG. 31 is a partial side elevational view of an alternate embodiment of an expandable sheath tube incorporating U-shaped expandable wires.
Figure 32:
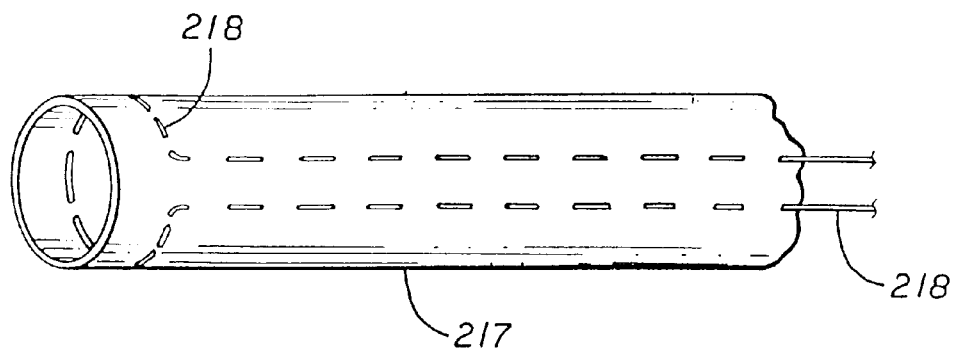
FIG. 32 is a partial side elevational view of an alternate embodiment of an expandable sheath tube incorporating a wire having a circular distal end.
Figure 33:
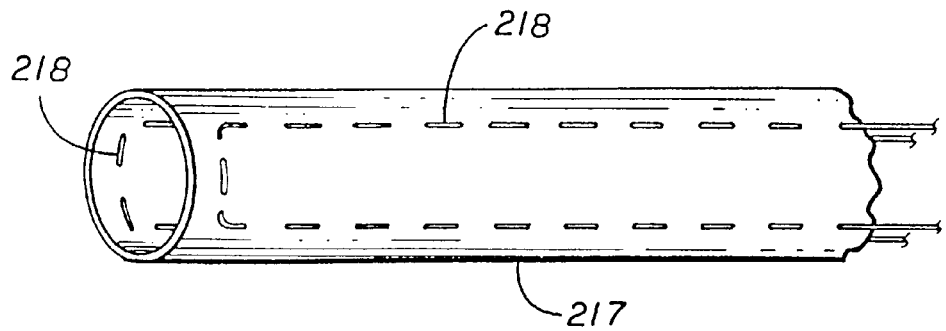
FIG. 33 is a partial side elevational view of an alternate embodiment of an expandable sheath tube incorporating an expandable wire including two half-circles at the distal end of the sheath tube.
Figure 34:
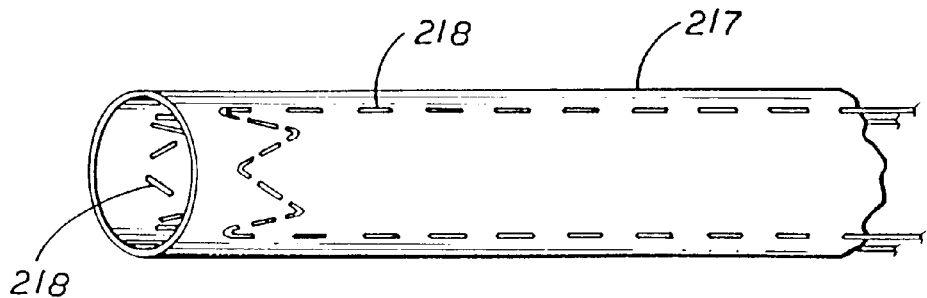
FIG. 34 is a partial side elevational view of an alternate embodiment of an expandable sheath tube incorporating expandable wires forming a "W" pattern at the distal end of the sheath tube.

Alternatively, the sheath tube 200 may be made of a Dacron graft 217 supported by longitudinally positioned nitinol wires 218 as shown in FIGS. 31–34. As shown in FIG. 31, the reinforcement wires may be run as tightly parallel U-shaped expansion means. Likewise, a single wire forming a circle at the distal end 202 of the sheath tube may be used. Similarly, two wires forming half-circles at the distal end may be used to reinforce and expand the sheath as shown in FIG. 33. Alternatively, the wires may form a "W" shape at the distal end of the sheath tube to provide radial expansion, as shown in FIG. 34.

As shown in FIG. 35, the large-diameter expandable sheath assembly 11 includes an introducer capsule 220. The reinforced sheath tube 200 is packed into the introducer capsule for deployment. The introducer capsule has a significantly less inner diameter than the outer diameter of the expanded sheath tube. The introducer capsule is configured such that it will peel away from the proximal end 201 of the reinforced sheath tube as the introducer capsule is withdrawn from the distal end 202 of the sheath tube. As the sheath introducer capsule is withdrawn, the reinforced sheath tube expands radially within the vessel.

As shown in FIG. 36, a removal capsule 225 may be fitted around the proximal 201 end of the reinforced sheath tube 200 to collapse the expanded sheath tube after the sheath tube has been deployed in a vessel. The removal capsule is configured with a lengthwise slit so it may be fitted over the proximal end of the secondary valve without having to fit over the backflow adapter 21. The removal capsule outer diameter is less than the outer diameter of the expanded sheath tube so as to radial collapse the sheath tube to a smaller diameter state. Once the reinforced sheath tube is collapsed, the removal capsule and sheath tube are then removed from the vessel. This retrieval reduces potential vessel trauma from removing a large diameter sheath.

Figure 37:
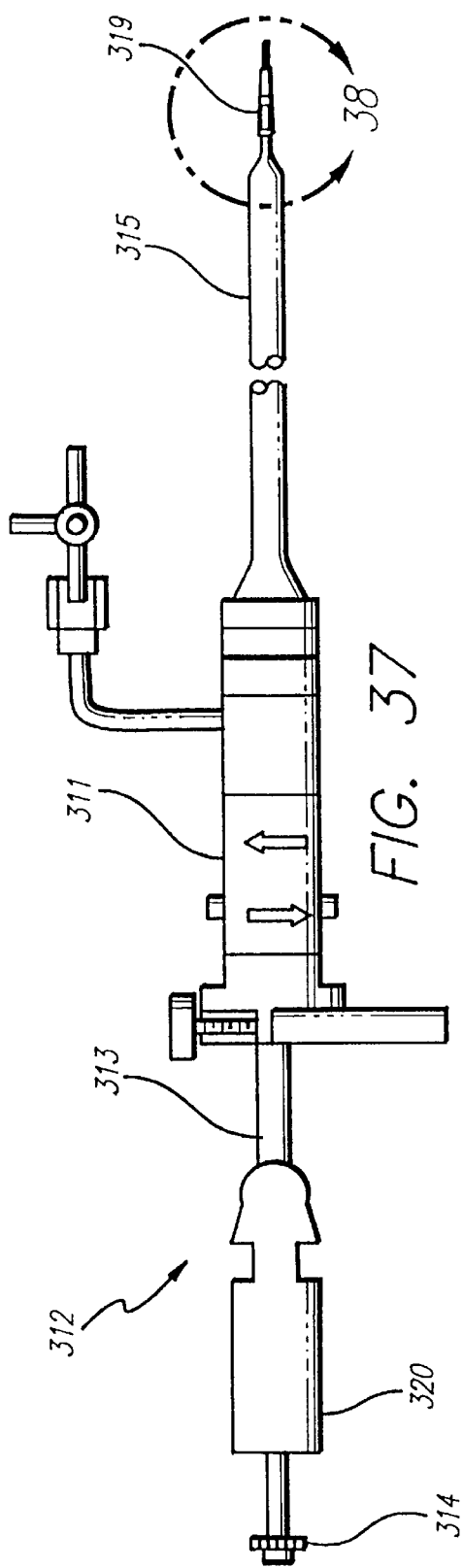
FIG. 37 is a side elevational view of an alternate embodiment of a large-diameter expandable sheath assembly incorporating the present invention.

An alternative preferred embodiment of the expandable sheath assembly characterized above is shown in FIG. 37. This embodiment operates in a similar fashion as described above, except to the extent described below. The sheath assembly 311 of this embodiment further includes a dilator assembly 312 for radially expanding the distal end of the sheath 315 which during introduction is laterally folded (see FIG. 38). The dilator assembly 312 has outer 313 and inner 314 coaxially oriented tubular members. The outer tubular member 313 (FIGS. 39, 40) has a length ranging from 250 mm to 410 mm, an outer diameter of approximately 8.2 mm and an internal bore having a diameter of 0.1 mm. The distal end 317 of the dilator assembly tapers to an outside diameter of 5.7 mm and an inside diameter of 2.0 mm and includes a small diameter tubular portion 318 extending therefrom. The small diameter tubular portion 318 has an outer diameter of 4.0 mm and an inner bore having a diameter on the order of 2.0 mm and is approximately 10 mm in length. The larger diameter portion of the outer tubular member 313 operates to dilate the sheath 315 during deployment of the sheath within a patient's vasculature.

Figure 41:
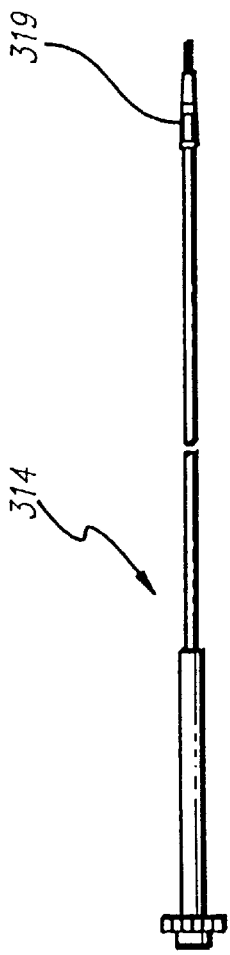
FIG. 41 is a side elevational view of the inner tubular member of the sheath assembly of FIG. 37.

The inner tubular member 314 (FIG. 41) carries a conically shaped cap 319, at the distal end of the member, into which the longitudinally folded, distal extremity of the sheath 315 is inserted. The conically shaped cap 319 and the folded sheath configuration of the sheath provides the assembly with a particularly useful overall profile, in that, the resulting overall tapered profile facilitates the insertion of the assembly within a patient's vasculature. The relatively smaller diameter cap 319 is designed for gaining easy access to the vessel and the tapered profile aides in smoothly advancing the assembly further within the vessel. The proximal end of the inner tubular member 314 is flanged or includes a conventional fitting which provides easy access to the interior of the member. The inner tubular member 314 is on the order of 500 mm in length, has an outer diameter of approximately 0.080 inches and an inner diameter of 0.042 inches. Being so configured, the inner tubular member 314 can slide within the internal bore of the outer tubular member 313 as well as slideably receive a conventional guide wire within its own internal bore. Moreover, when configured coaxially within the outer tubular member 313, the distal and proximal ends of the inner tubular member extend beyond the corresponding extremities of the outer tubular member 313.

Figure 38:
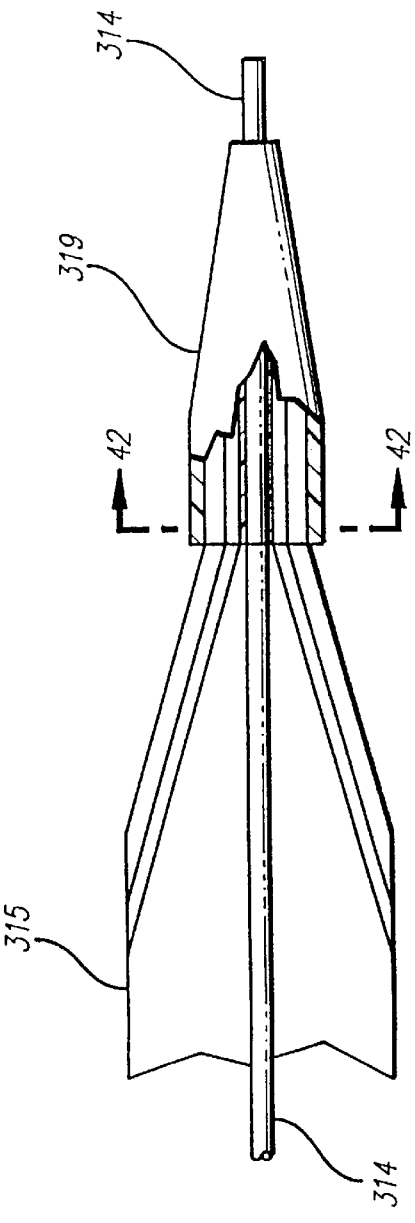
FIG. 38 is an enlarged side elevational view of the distal end of the sheath assembly of FIG. 37 at 38 depicting the end cap assembly in partial cross-sectional view.
Figure 42:
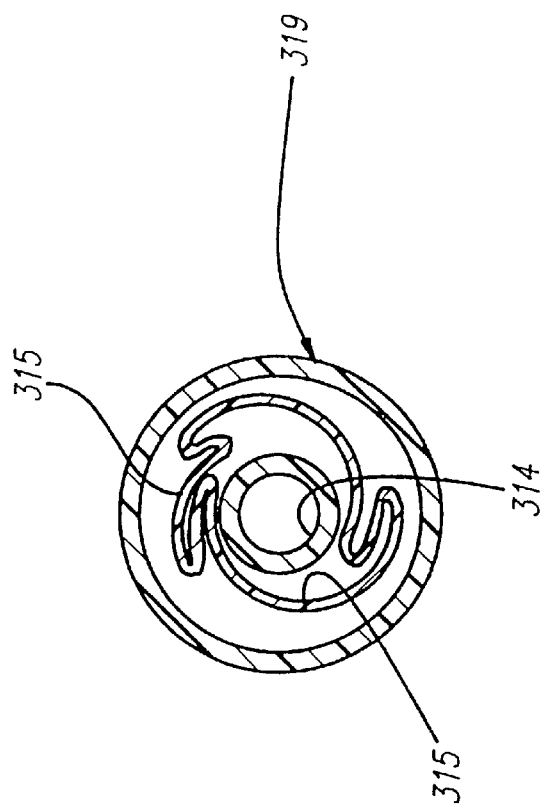
FIG. 42 is an enlarged cross-sectional view of the end cap assembly of FIG. 38 at 42—42.

As shown in FIG. 38, the outer profile of the cap 319 is tapered towards the distal end of the inner tubular member 314. The cap is approximately 30 mm in length and tapers from an outside diameter of 5.7 mm at its proximal end to 2.0 mm at its distal end. The inside of the cap 319 likewise has a diameter which tapers from 4.5 mm to 2.0 mm. The proximal end of the cap 319, as shown more particularly in FIG. 42, defines a cavity into which the folded distal end of the sheath 315 is received. The proximal end of the cap 319 is further shaped so that the outer diameter of the cap 319 matches the outer diameter of the distal end of the outer tubular member 313 to provide a smooth tapered transition when the cap 319 abuts against the distal end 317 of the outer tubular member 313. This smooth transitional surface prevents the cap 319 from catching upon the sheath 315 when the dilator assembly 312 is removed from the sheath 315 after the sheath 315 is deployed (See also FIG. 47).

Figure 43:
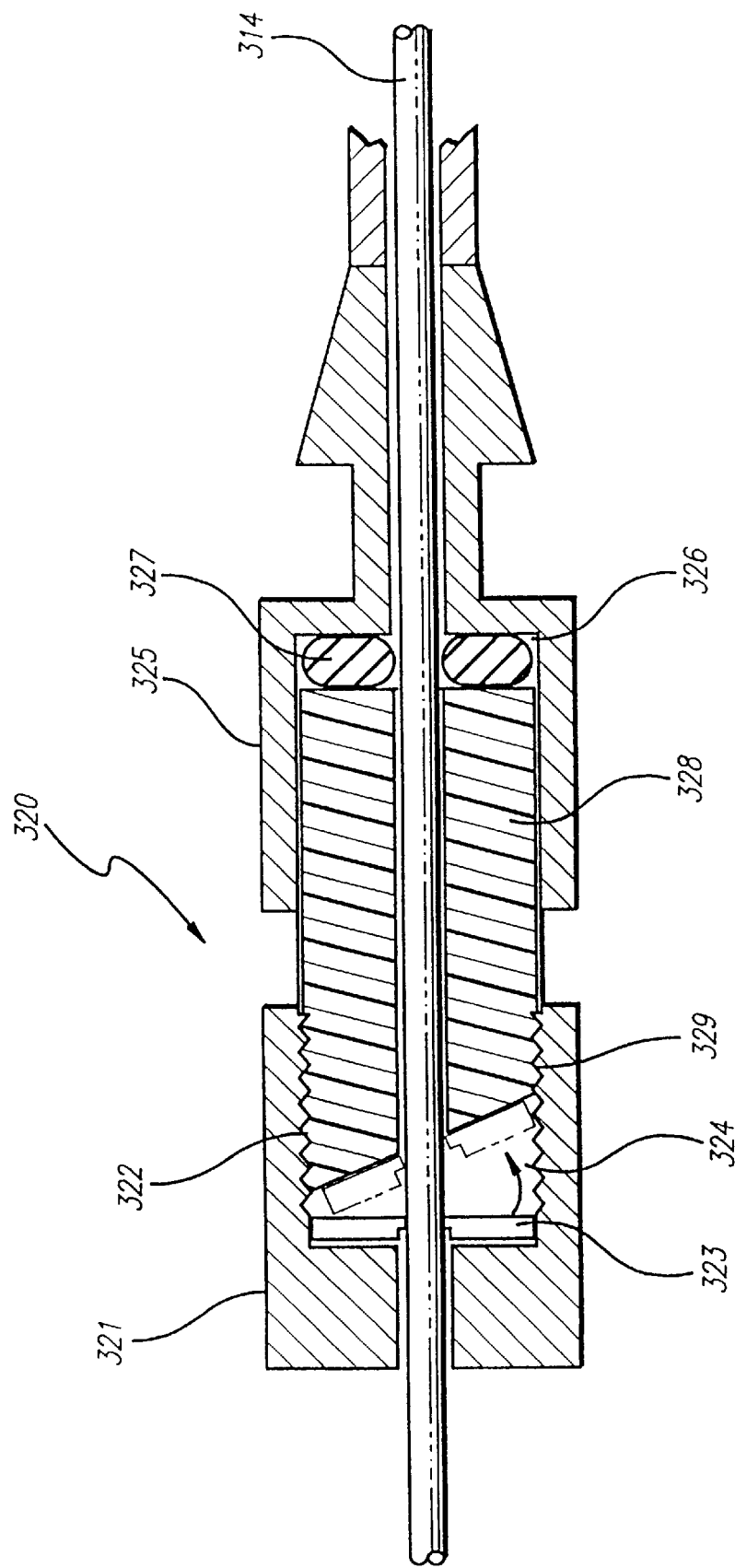
FIG. 43 is an enlarged cross-sectional side elevational view of the proximal end of the sheath assembly depicting the locking mechanism of the embodiment of FIG. 37.

The expandable sheath assembly may also include a one-way locking mechanism 320 which operates to allow the inner tubular member 314 to move freely in the proximal direction relative to the outer tubular member 313 (See FIG. 43). The locking mechanism assembly 320 further operates to resist movement by the inner tubular member 314 in the distal direction with respect to the outer tubular member 313. This is important for the purposes of control and safety. The locking mechanism assembly 320 provides the operator with assurance that the inner tubular member 314 will not inadvertently move farther than desired within a patient's vasculature as well as provides a means for keeping track of the general longitudinal relationship between the outer and inner tubular members 313, 314.

The locking mechanism assembly 320, depicted in FIG. 43, is mounted near the proximal end of the outer tubular member 313 and embodies a proximal housing shell 321, a distal housing shell 325 and an inner member 328. When assembled the proximal and distal housing shells 321, 325 and inner member 328 define a chamber area 324. The proximal housing shell 321 further includes a proximal wall with an opening through which the inner tubular member 314 passes. The proximal wall of the proximal housing 321 is substantially perpendicular to the longitudinal axis of the inner tubular member 314 inserted through the proximal housing 321. The inner circumference of the chamber area 324 of the proximal housing 321 includes threads 322, as shown in FIG. 43.

Configured within the chamber area 324 is a washer, or like structure 323, that has a hole through which the inner tubular member 314 passes. The size of the hole opening of the washer 323 is chosen so that the inner tubular member 314 moves freely therethrough when the washer is substantially perpendicular to a longitudinal axis of the inner tubular member 314. When the washer is oriented at an angle that is not perpendicular to the longitudinal axis of the inner tubular member 314, the washer locks onto the inner tubular member 314.

The distal housing shell 325 of the locking mechanism assembly 320 has a distal wall with an opening through which the inner tubular member 314 passes. The proximal end of the distal housing shell 325 is open forming a hollow shell. It is into this hollow shell that the inner member 328 of the locking mechanism assembly 320 is inserted and secured as a press or sweat fit, or is secured therein by way of another equivalent means, to the inner wall of the distal housing shell 325. A cavity 326 defined by the distal housing shell 325 and inner member 328 is provided and is adapted to receive an O-ring 327 for sealing the inner tubular member 314 within the locking mechanism assembly 320 from a patient's vasculature.

The inner member 328 is configured with a hole through its entire length for allowing the passing of the inner tubular member 314 through the inner member 328. At least a portion of the outer circumference of the proximal half of the inner member 328 includes threads 329, as shown in FIG. 43. The diameter, outer circumference and respective threads 329 of the inner member 328 correspond to the inner diameter, circumference and threads 322 of the proximal housing shell 321. Further, the proximal end of the inner member is cut at a 40° angle.

When the proximal housing shell 321 is screwed onto the threads of the inner member 328, the chamber area 324 in the proximal housing 321 becomes smaller until the most proximal portion of the 40° angled cut proximal end of the inner member 328 is nearly touching the upper portion of the locking washer 323, as shown in FIG. 43. In this configuration, any attempt to push the inner tubular member in the distal direction, (i.e., towards the patient), will force the locking washer 323 against the 40° cut proximal end surface of the inner member 328.

Therefore, when the inner tubular member 314 is pulled in the proximal direction, the washer 323 is forced against the proximal wall of the proximal housing 321 and is substantially perpendicular to the longitudinal axis of the inner tubular member 314, thereby allowing the inner tubular member 314 to pass freely through the locking mechanism assembly 320. When the inner tubular member 314 is pushed in the distal direction the washer 323 is forced parallel against the 40° angled proximal wall of the inner member 328. The washer 323 is now oriented at an angle to the inner tubular member 314 which operates to lock the washer 323 to the inner tubular member 314. With the washer 323 locked onto the inner tubular member 314 the inner tubular member 314 is restricted from any movement in the distal direction.

An alternate configuration of the locking mechanism assembly 320, not shown, would encompass the distal housing shell 325 and inner member 328 as a single machined member which would then mate with the proximal housing shell 321 as described above.

There is shown in FIGS. 44–47 steps performed in accomplishing the deployment of the expandable sheath introducer assembly 311 when using the alternate embodiment described above. In FIG. 44, the sheath introducer assembly 311 is shown with the sheath 315 folded into the cavity at the proximal end of the end cap 319. The folded extremity of the sheath 315 is positioned distally with respect to the distal end of the outer tubular member 313. In this configuration, the sheath assembly 311 is ready for insertion into the vascular system of a patient (not shown).

In FIG. 45, the sheath 315 is deployed by moving the outer and inner tubular members 313 and 314, as a unit, in a distal direction. Such movement of the inner tubular member 314 removes the end cap 319 from the tip of the longitudinally folded distal end of the sheath 315. Simultaneous movement of the outer tubular member 313 brings the larger outer diameter of the outer tubular member into engagement with the folded distal end of the sheath, thereby dilating the folds of the sheath.

Figure 46:
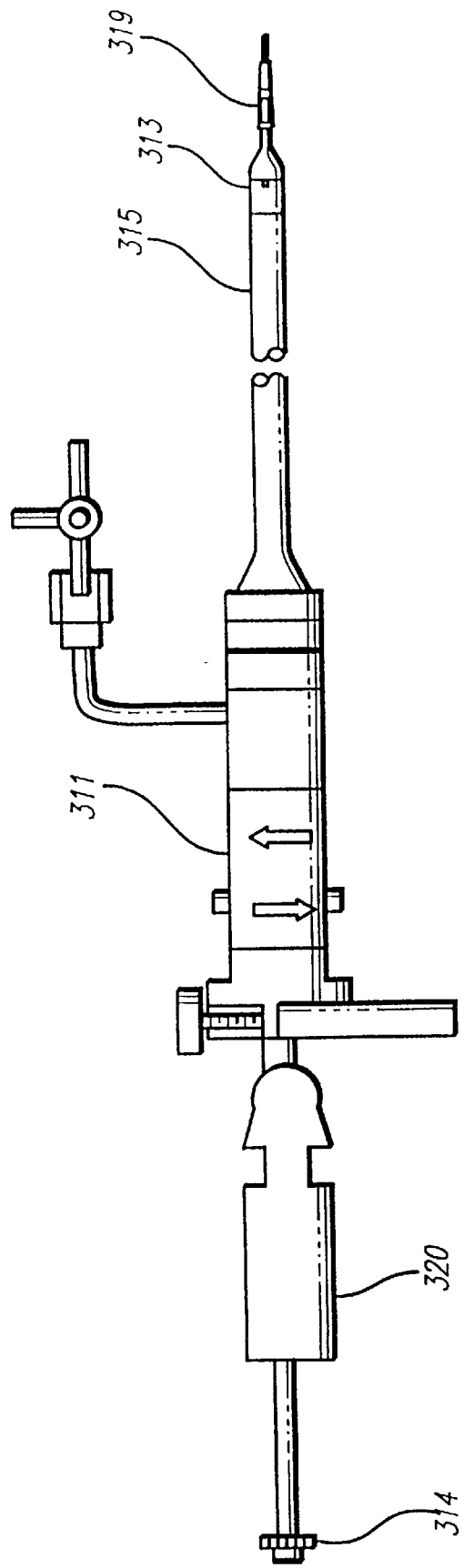
FIG. 46 is a side elevational view of the embodiment of FIG. 45 showing the inner tubular member moved proximally.
Figure 47:
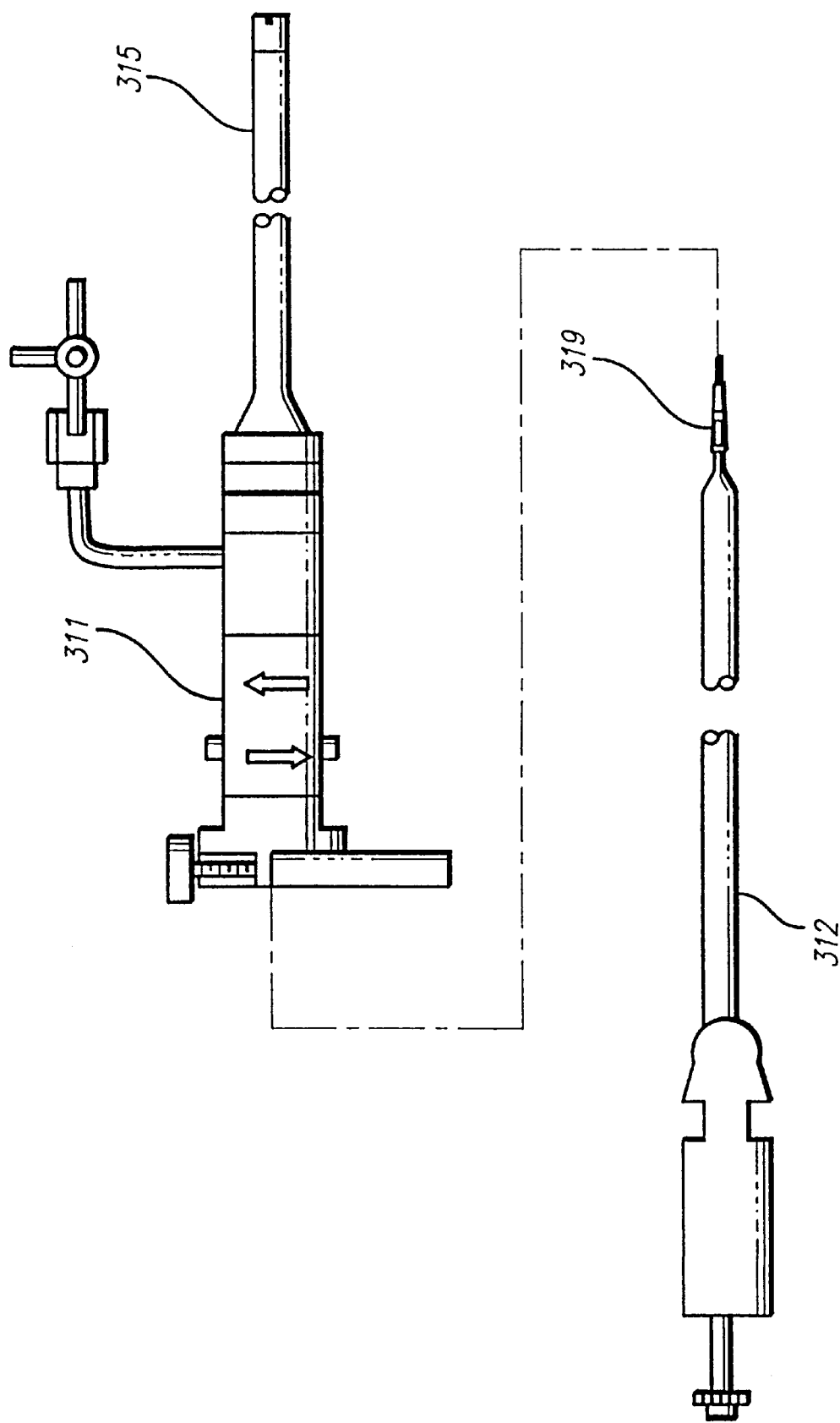
FIG. 47 is a side elevational view of the embodiment of FIG. 46 depicting the final configuration of the assembly during a sheath insertion procedure into a vascular system.

As shown in FIG. 46, the inner tubular member 314 is then pulled in the proximal direction to abut the end cap 319 against the distal end of the outer tubular member 313 to thereby prepare the dilator assembly 312 for easy removal from the the sheath 315. Finally, as depicted in FIG. 47, the dilator assembly 312 is thereafter removed from the sheath assembly 311. In this configuration, the sheath assembly 312 is used to insert catheters and other instruments into a patient's vascular system.

While several particular forms of the invention have been illustrated and described, it will be apparent that various modifications can be made without departing from the spirit and scope of the invention. For example, references to materials of construction and specific dimensions are also not intended to be limiting in any manner and other materials and dimensions could be substituted and remain within the spirit and scope of the invention. Accordingly, it is not intended that the invention be limited, except as by the appended claims.

What is claimed is:

1. A large-diameter expandable sheath for use in introducing a catheter into a corporeal vessel, comprising:

an elongate sheath tube formed of a flexible material having proximal and distal extremities and having a passage extending therethrough of a maximum predetermined diameter;

the distal extremity of said sheath tube being folded longitudinally to a smaller folded diameter;

a backflow adapter secured to the proximal extremity of said sheath tube;

said backflow adapter having a central opening therein in registration with the passage in said sheath tube and having a valve disposed in the central opening of said backflow adapter and movable between open and closed positions;

wherein the valve when open permits the catheter to be inserted into said sheath tube and when closed forms a hemostatic seal about the catheter;

wherein the valve is in the form of a cylindrical member formed of a flexible material and having a bore therein in registration with the central opening of said backflow adapter;

said backflow adapter having a rotatable device, said rotatable device configured to engage the opposite ends of the cylindrical member for causing relative rotation between the ends of the cylindrical member to cause the cylindrical member to be twisted to close the bore extending through the cylindrical member; and said rotatable device includes a retaining ring, a sheath tube adapter secured to opposite ends of the cylindrical member, a fixing device that fixes the sheath tube adapter to prevent rotation of the same within said backflow adapter, and a first sub-component that rotates the retaining ring with respect to the sheath tube adapter.

2. The sheath of claim 1, wherein said rotatable device includes a ring gear secured to said retaining ring and a rack, said rack drives said ring gear to cause rotation of the same.

3. The sheath of claim 2, further comprising a yieldable device that engages said rack and urges said rack into a position wherein said cylindrical member is moved to provide a normally closed valve device.

4. The sheath of claim 3, wherein said rack extends tangentially through said body together with an actuator carried by the rack adapted to be engaged by the fingers of the hand that operates to move against the force of the yieldable device to move the normally closed valve device to an open position.

5. The sheath of claim 4, further comprising a stabilizer rod slidably mounted within said body parallel to said rack and secured to said actuator.

6. The sheath of claim 5, further comprising a second sub-component, said second sub-component carried by the rack and adapted to prevent said yieldable device from pulling said rack out of engagement with said cylindrical member.

7. A large-diameter expandable sheath for use in introducing a catheter into a corporeal vessel, comprising:

an elongate sheath tube formed of a flexible material having proximal and distal extremities and having a passage extending therethrough of a maximum predetermined diameter;

the distal extremity of said sheath tube being folded longitudinally to a smaller folded diameter;

a backflow adapter having a central opening therein in registration with the passage in said sheath rube and having a valve disposed in the central opening of said backflow adapter and movable between open and closed positions;

wherein the valve when open permits the catheter to be inserted into said sheath tube and when closed forms a hemostatic seal about the catheter; and a sheath introducer disposed in the passage of said sheath tube to form an assembly, said sheath introducer having a distal extremity extending beyond the proximal extremity of said sheath tube and a dilator mounted on the distal extremity of said sheath introducer with has a diameter greater than the folded diameter of said sheath tube.

8. A large-diameter expandable sheath tube assembly for use in a corporeal vessel, comprising:

an elongate flexible sheath tube having proximal and distal extremities and having a passage extending therethrough of a maximum diameter;

a backflow adapter mounted on the proximal extremity of said sheath tube;

a sheath introducer disposed in said backflow adapter and extending through the passage in said sheath tube;

said sheath introducer comprising an elongate tubular member having a proximal extremity and a distal extremity having a reduced diameter from the proximal extremity;

the distal extremity of said sheath tube being folded over the distal extremity of the elongate tubular member of said sheath introducer to a folded diameter;

said sheath introducer having a sleeve that covers the folded distal extremity of said sheath tube to prevent the folded distal extremity of the sheath tube from causing trauma to the vessel when the sheath tube is introduced into the vessel;

a securing device that secures said sleeve on the elongate tubular member of said sheath introducer so that said sheath introducer can be pushed distally with respect to said sheath tube to cause said sleeve to be removed from the distal extremity of said sheath tube to permit said sheath tube to expand and to push the proximal extremity of said sheath introducer through the distal extremity of said sheath tube to expand said sheath tube; and said securing device includes a length of shrink tubing extending over said sleeve and having a diameter greater than said sleeve.

9. The assembly of claim 8, further comprising a preventing device carried by the distal extremity of the sheath introducer to prevent the shrink tubing from being separated from the distal extremity of the sheath introducer.

10. A sheath tube introducer, comprising:

a flexible elongate tubular member having proximal and distal extremities;

a fitting positioned at the proximal extremity of said tubular member;

a sleeve positioned at the distal extremity of said tubular member;

said sleeve having a proximal expandable extremity and a distal extremity;

a securing device that prevents the distal extremity of said sleeve from being separated from the distal extremity of said tubular member; and said securing device includes a length of shrink tubing mounted on said sleeve.

11. The sheath introducer of claim 10, wherein the proximal extremity of the flexible elongate tubular member is of greater diameter to provide additional rigidity to the flexible elongate tubular member and to provide a dilator that dilates the distal extremity of the sheath tube.

12. A sheath tube introducer, comprising:
   a flexible elongate tubular member having proximal and distal extremities;
   a fitting positioned at the proximal extremity of said tubular member;
   a sleeve positioned at the distal extremity of said tubular member;
   said sleeve having a proximal expandable extremity and a distal extremity;
   a securing device that prevents the distal extremity of said sleeve from being separated from the distal extremity of said tubular member; and
   said tubular member having a flow passage therein together with an opening formed in said tubular member proximal of the proximal extremity of said sleeve and in communication with the flow passage.

13. A backflow adapter having a body with a central opening in fluid communication with a sheath tube, comprising:
   a first diaphragm disposed in the central opening of said backflow adapter, said first diaphragm having a first end and a second end and being movable between open and closed positions;
   a first retainer that engages said first diaphragm for causing relative rotation between the ends of said first diaphragm;
   a second diaphragm disposed in the central opening of said backflow adapter and adjacent the second end of said first diaphragm, said second diaphragm having a first end and a second end and being movable between open and closed positions; and
   a second retainer that engages said second diaphragm for causing relative rotation between the ends of said second diaphragm.

14. The backflow adapter of claim 13, wherein said second retainer includes a gear secured to the second diaphragm and a rack for driving the gear to cause rotation of the second diaphragm.

15. The backflow adaptor of claim 14, wherein the second retainer further comprises a biasing device that urges the rack into a position wherein the second diaphragm is rotated to a closed position.

16. The backflow adaptor of claim 15, wherein the second retainer comprises an actuator carried by the rack for moving the rack against the force of the biasing device to move the second diaphragm to an open position.

17. The backflow adaptor of claim 16, wherein the second retainer further comprises a stabilizer rod slidably mounted parallel to the rack and secured to the actuator.

18. The backflow adapter of claim 17, further comprising a sheath tube adapter secured to the body of said backflow adapter and secured to a sheath tube so as to prevent rotation of said sheath tube adapter when either said first diaphragm or said second diaphragm are rotated within the body of said backflow adapter.

* * * * *